US006984210B2

(12) United States Patent
Chambers et al.

(10) Patent No.: US 6,984,210 B2
(45) Date of Patent: Jan. 10, 2006

(54) DIAGNOSTIC ANALYSIS OF ULTRASOUND DATA

(75) Inventors: David H. Chambers, Livermore, CA (US); Jeffrey Mast, Loveland, CO (US); Stephen G. Azevedo, Livermore, CA (US); Frank Wuebbeling, Billerbeck (DE); Frank Natterer, Muenster (DE); Neb Duric, Albuquerque, NM (US); Peter J. Littrup, Bloomfield, MI (US); Earle Holsapple, Grosse Pointe Farms, MI (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 200 days.

(21) Appl. No.: 10/323,467

(22) Filed: Dec. 18, 2002

(65) Prior Publication Data

US 2004/0122325 A1 Jun. 24, 2004

(51) Int. Cl.
*A61B 8/00* (2006.01)

(52) U.S. Cl. .................................................... 600/443
(58) Field of Classification Search ......... 600/437–482; 73/625–626; 367/7, 11, 130, 138
See application file for complete search history.

(56) References Cited

U.S. PATENT DOCUMENTS

| 3,154,067 A | 10/1964 | Stenstrom et al. |
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A * | 2/1978 | Glover ........................ 73/607 |
| 4,105,018 A | 8/1978 | Greenleaf et al. |
| 4,222,274 A | 9/1980 | Johnson |
| 4,317,369 A | 3/1982 | Johnson |
| 4,515,165 A | 5/1985 | Carroll |
| 4,542,744 A | 9/1985 | Barnes et al. |
| 4,564,019 A | 1/1986 | Miwa |

(Continued)

FOREIGN PATENT DOCUMENTS

| AU | A-344332/95 | 2/1996 |
| EP | 0 351 610 A2 | 1/1990 |
| EP | 0 538 241 B1 | 4/1993 |
| EP | 0 538 241 A2 | 4/1993 |
| EP | 0 284 055 B1 | 9/1993 |
| EP | 0 609 922 A2 | 8/1994 |
| EP | 0 661 029 A1 | 7/1995 |
| EP | 0 774 276 A2 | 5/1997 |

OTHER PUBLICATIONS

Andre, et al. "A New Consideration of Difraction Computed Tomography for Breast Imaging: Studies in Phantoms and Patients" *Acoustical Imaging,* J.P. Jones, Plenum Press, New York (1995), pp. 379–390.

Borup, et al. "Nonperturbative Diffraction Tomography Via Gauss–Newton Iteration Applied to the Scattering Integral Equation" *Ultrasonic Imaging,* Academic Press, Inc. (1992) vol. 14, pp. 69–85.

(Continued)

*Primary Examiner*—Ali Imam
(74) *Attorney, Agent, or Firm*—Townsend and Townsend and Crew LLP

(57) ABSTRACT

A method and apparatus are provided for investigating tissue in which acoustic data are derived from scattering a plurality of pulsed spherical or cylindrical acoustic waves from a plurality of transmission elements through the tissue to a plurality of receiving elements. The acoustic data, which include a mix of reflected and transmitted acoustic waves, are received and digitized, and a representation of a portion of the tissue is generated from the digitized acoustic data.

32 Claims, 23 Drawing Sheets

U.S. PATENT DOCUMENTS

| | | |
|---|---|---|
| 4,662,222 A | 5/1987 | Johnson |
| 4,671,256 A | 6/1987 | Lemelson |
| 4,855,911 A | 8/1989 | Lele et al. |
| 4,858,124 A | 8/1989 | Lizzi et al. |
| 4,917,096 A | 4/1990 | Englehart et al. |
| 4,941,474 A | 7/1990 | Pratt, Jr. |
| 5,003,979 A | 4/1991 | Merickel et al. |
| 5,029,476 A | 7/1991 | Metala |
| RE33,672 E | 8/1991 | Miwa |
| 5,143,069 A | 9/1992 | Kwon |
| 5,158,071 A | 10/1992 | Umemura et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,268,876 A * | 12/1993 | Rachlin ..................... 367/7 |
| 5,269,309 A | 12/1993 | Fort et al. |
| 5,280,788 A | 1/1994 | Janes et al. |
| 5,304,173 A | 4/1994 | Kittrell et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,413,108 A | 5/1995 | Alfano |
| 5,415,164 A | 5/1995 | Faupel |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,596,992 A | 1/1997 | Haaland et al. |
| 5,606,971 A | 3/1997 | Sarvazyan |
| 5,620,479 A | 4/1997 | Diederich |
| 5,640,956 A | 6/1997 | Getzinger et al. |
| 5,643,179 A | 7/1997 | Fujimoto |
| 5,664,573 A | 9/1997 | Shmulewitz |
| 5,678,565 A | 10/1997 | Sarvazyan |
| 5,722,411 A | 3/1998 | Suzuki et al. |
| 5,743,863 A | 4/1998 | Chapelon |
| 5,762,066 A | 6/1998 | Law et al. |
| 5,766,129 A | 6/1998 | Mochizuki |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,833,614 A | 11/1998 | Dodd et al. |
| 5,846,202 A | 12/1998 | Ramamurthy et al. |
| 5,865,167 A | 2/1999 | Godik |
| 5,865,743 A | 2/1999 | Godik |
| 5,891,619 A | 4/1999 | Zakim et al. |
| 6,002,958 A | 12/1999 | Godik |
| 6,005,916 A | 12/1999 | Johnson et al. |
| 6,109,270 A | 8/2000 | Mah et al. |
| 6,117,080 A | 9/2000 | Schwartz |
| 6,135,960 A | 10/2000 | Holmberg |
| 6,149,441 A | 11/2000 | Pellegrino |
| 6,296,489 B1 | 10/2001 | Blass et al. |
| 2002/0131551 A1 | 9/2002 | Johnson |

OTHER PUBLICATIONS

Chelfouh, et al. "Characterization of Urinary Calculi: In Vitro of 'Twinkling Artifact' Revealed by Color–Flow Sonography" *American Journal of Roentgenology* (1998) vol. 171, pp. 1055–1060.

Dean, Stanley R., "The Radon Transform and Some of Its Applications" *Krieger Publishing Company, Malabar, Florida* (1993).

Greenleaf, J.F. "Tissue Characterization with Ultrasound: vol. II: Results and Applications" *CRC Press, Inc., Boca Raton, Florida,* pp. 95–122.

Greenleaf, J.F., et al. "Introduction to Computer Ultrasound Tomography" *Computed Aided Tomography and Ultrasonics in Medicine,* North–Holland, (1970); pp. 125–136.

Greenleaf, J.F., et al. "Multidimensional Visualization of Ultrasonic Images" *J. Acoust. Soc. Amer.* vol. 95 (2902), (1994).

Hebden, et al. "Acoustically Modulated Electrical Impedance Tomography" *Proceedings of the SPIE,* vol. 1231 (1990); pp. 7–14.

Jellins, J. "Breast Tissue Characterizations" *Tissue Characterization with Ultrasound.* vol. II, CRC Press, (1986); pp. 95–122.

Johnson, et al. "Modeling of Inverse Scattering and Other Tomographic Algorithms in Conjunction with Wide Bandwidth Acoustic Transducer Arrays for Towed or Autonomous Sub–bottom Imaging Systems" *Proceedings of Mastering the Oceans Through Technology, Oceans* Newport, Rhode Island, USA, (Oct. 26–29, 1992), pp. 294–299.

Johnson, et al. "Comparison of Inverse Scattering and Other Tomographic Imaging Algorithms Using Simulated and Tank Data for Modeling Subbottom Imaging Systems" IEEE Oceans '93 Symposium, Nov. 1993, vol. 1, pp. 458–492 (1993).

Louvar, et al. "Correlation of Color Doppler Flow in the Prostate with Tissue Microvascularity" *Cancer,* (Jul. 1998) vol. 1:83 (1); pp. 135–140.

Nelson, et al. "Interactive Acquisition, Analysis and Visualization of Songraphic Volume Data" *International Journal of Imaging Systems and Technology* (1997) vol. 8(26), pp. 26–37.

Sehgal, et al. "Visualization of Breast Calcification by Acoustic Resonance Imaging" *Radiology Supplement,* 84th Scientific Assembly and Annual Meeting, Nov. 29–Dec. 4, 1998 presented in McCormick Place, Chicago, Illinois (1998) vol. 209, listing: 1150.

Shi, et al. "Effects of Pressure Changes on Harmonic and Subharmonic Response of US Contrast Microbubbles" 84th Scientific Assembly and Annual Meeting, Nov. 29–Dec. 4, 1998 presented in McCormick Place, Chicago, Illinois (1998) vol. 209, listing: 1154.

Wiskin, et al. "Full Inverse Scattering vs. Born–like Approximation for Imaging In a Stratified Ocean" *Proc. of Engineering in harmony with the Ocean (Oceans '93 ),* Victoria, British Columbia, Oct. 1993.

* cited by examiner

DIAGNOSTIC ANALYSIS OF ULTRASOUND DATA

CROSS-REFERENCES TO RELATED APPLICATIONS

This application is being filed concurrently with related U.S. patent application Ser. No. 10/323,354 "COMPUTERIZED ULTRASOUND RISK EVALUATION SYSTEM," by Neb Duric et al. This application is also related to commonly assigned U.S. Pat. No. 6,385,474 entitled "METHOD AND APPARATUS FOR HIGH-RESOLUTION DETECTION AND CHARACTERIZATION OF MEDICAL PATHOLOGIES," filed Mar. 19, 1999 by John D. Rather et al., the entire disclosure of which is herein incorporated by reference for all purposes.

STATEMENT AS TO RIGHTS TO INVENTIONS MADE UNDER FEDERALLY SPONSORED RESEARCH OR DEVELOPMENT

The Government has rights in this invention pursuant to U.S. Dept. of Energy Work for Others Agreement L-8420.

BACKGROUND OF THE INVENTION

The present invention relates generally to imaging systems. More particularly, the present invention relates to ultrasound imaging systems.

There are a number of disadvantages associated with various imaging systems that are currently in use, particularly when used for medical applications. For example, a number of imaging techniques, such as x-ray imaging, mammography, and computed tomographic (CT) scans, use ionizing radiation that presents a risk of cell mutation when used medically. Also, CT scans and magnetic resonance imaging (MRI) techniques both involve procedures that are relatively expensive, a factor that by itself acts to some degree to limit their use. A significant disadvantage of methods such as mammography is that they rely on two-dimensional images that may disguise three-dimensional structure information that can be critical for diagnosis.

As an alternative to these imaging technologies, the medical community has looked to ultrasound for providing a safe, low-cost, high-resolution imaging tool. There are, however, significant limitations to conventional ultrasound, which may be used in A or B scanning modes. Such modes are distinguished by the fact that an A scan is purely one dimensional while a B scan produces a two-dimensional image. As a result, imaging applications tend to use ultrasonic B scanning. In such conventional ultrasound analysis, a small array of elements is moved by hand in contact with tissue under study. The array sends out waves that reflect from tissues back to the same array. This arrangement results in two major drawbacks. First, ultrasonic B scans do not provide information on the properties of the materials themselves; rather, they provide information only on the reflectivity of the boundaries between different types of materials. Second, the array is incapable of capturing scattered radiation except that reflected back to the hand held sensing array. Considerable information exists, however, in the transmitted waves, but this information is neither captured nor used diagnostically in conventional ultrasonic B scans.

There is thus a need for an apparatus and method that provides improved imaging, particularly as applied to medical applications.

BRIEF SUMMARY OF THE INVENTION

Thus, a method and apparatus are provided for investigating tissue. In one embodiment, acoustic data are derived from scattering a plurality of pulsed spherical or cylindrical acoustic waves from a plurality of transmission elements through the tissue to a plurality of receiving elements. The acoustic data, which include a mix of reflected and transmitted acoustic waves, are received and digitized, and a representation of a portion of the tissue is generated from the digitized acoustic data. Generating the representation may comprise removing a direct coupling pulse from the received acoustic data. In different embodiments, generating the representation may comprise performing a time-series analysis of the digitized acoustic data or may comprise performing a frequency-series analysis of the digitized acoustic data.

Various methods may be used for generating the representation. For example, in one embodiment a full-aperture tomographic method is used in which a wave path is computed for a time delay for each pair of transmitting and receiving elements. The wave paths are summed to derive an image representation of the portion of the tissue.

In another embodiment, a quantitative full-aperture tomographic method is used. The digitized acoustic data are organized according to at least two independent dimensions. The digitized data are then fit numerically to an expression relating the expected intensity variation in terms of physical quantities having different dependencies in the at least two independent dimensions. The physical quantities may comprise, for example, a compressibility contrast and a density contrast.

In a further embodiment, a diffraction tomographic method is used in which the digitized acoustic data are converted to a frequency domain. Scattered-field Fourier components are extracted from the converted data, from which a complex potential is calculated. Physical properties of the portion of the tissue, such as sound speed and attenuation, are derived from the complex potential.

In still another embodiment, a full-wave adjoint tomographic method is used. An initial tissue model of the portion of the tissue is selected, perhaps by using one of the previously discussed methods. Wave propagation through the tissue model is simulated with a wave-propagation model to determine simulated data. The simulated data and the digitized acoustic data are used to calculate a residual, which is backpropagated to update the tissue model. The simulated wave propagation and backpropagation are repeated iteratively until the residual has a magnitude less than a predefined threshold.

The compressibility of the tissue may be determined by comparing sets of acoustic data derived from two insonifications of the tissue. In one embodiment, the two insonifications are separated by a mechanical compression of the tissue. In another embodiment, the second insonification acts to compress the tissue. A representation of the tissue may be generated by correlating an acoustic property of the tissue with a difference between two compression modes by insonifying the tissue with each of the compression modes and measuring respective sets of acoustic data.

The methods of the invention may be performed as part of the function of a control system, which generally includes a front end for interfacing with a sensor system. The front end is adapted to receive acoustic data derived from scattering a radiation pattern. The control system also includes an analog-to-digital converter for digitizing the acoustic data and includes a reconstruction element. The reconstruction element is configured to perform the methods described.

BRIEF DESCRIPTION OF THE DRAWINGS

The patent or application file contains at least one drawing executed in color. Copies of this patent or patent application publication with color drawings will be provided by the Office upon request and payment of the necessary fee.

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and is enclosed in parentheses to denote one of multiple similar components. When reference is made to a reference numeral without specification to an existing sublabel, it is intended to refer to all such multiple similar components.

DETAILED DESCRIPTION OF THE INVENTION

1. Overview

Figure 1A:
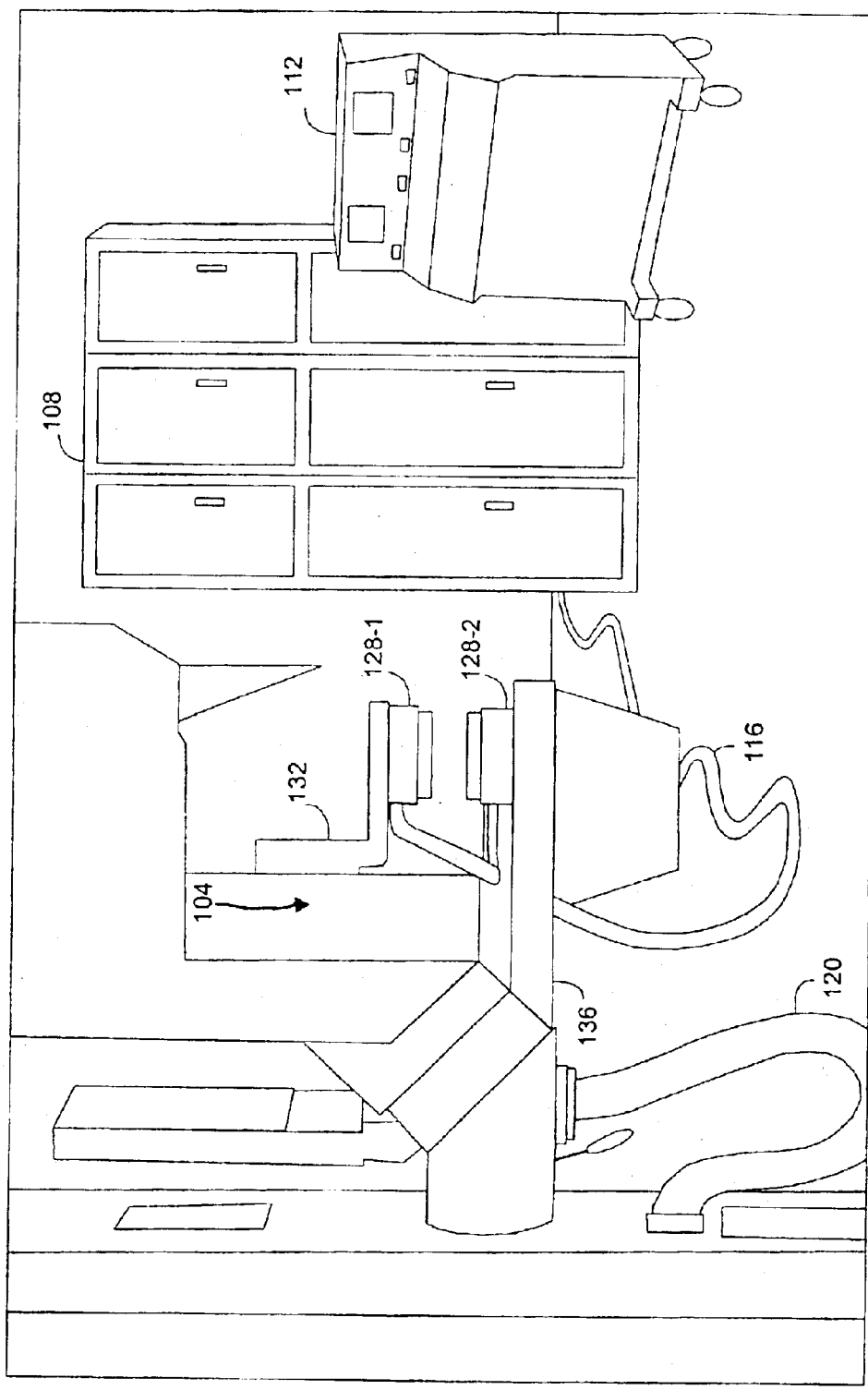
FIGS. 1A and 1B provide an overview of a system according to one embodiment of the invention, illustrated as a physical embodiment in FIG. 1A and illustrated schematically in FIG. 1B.
Figure 1B:
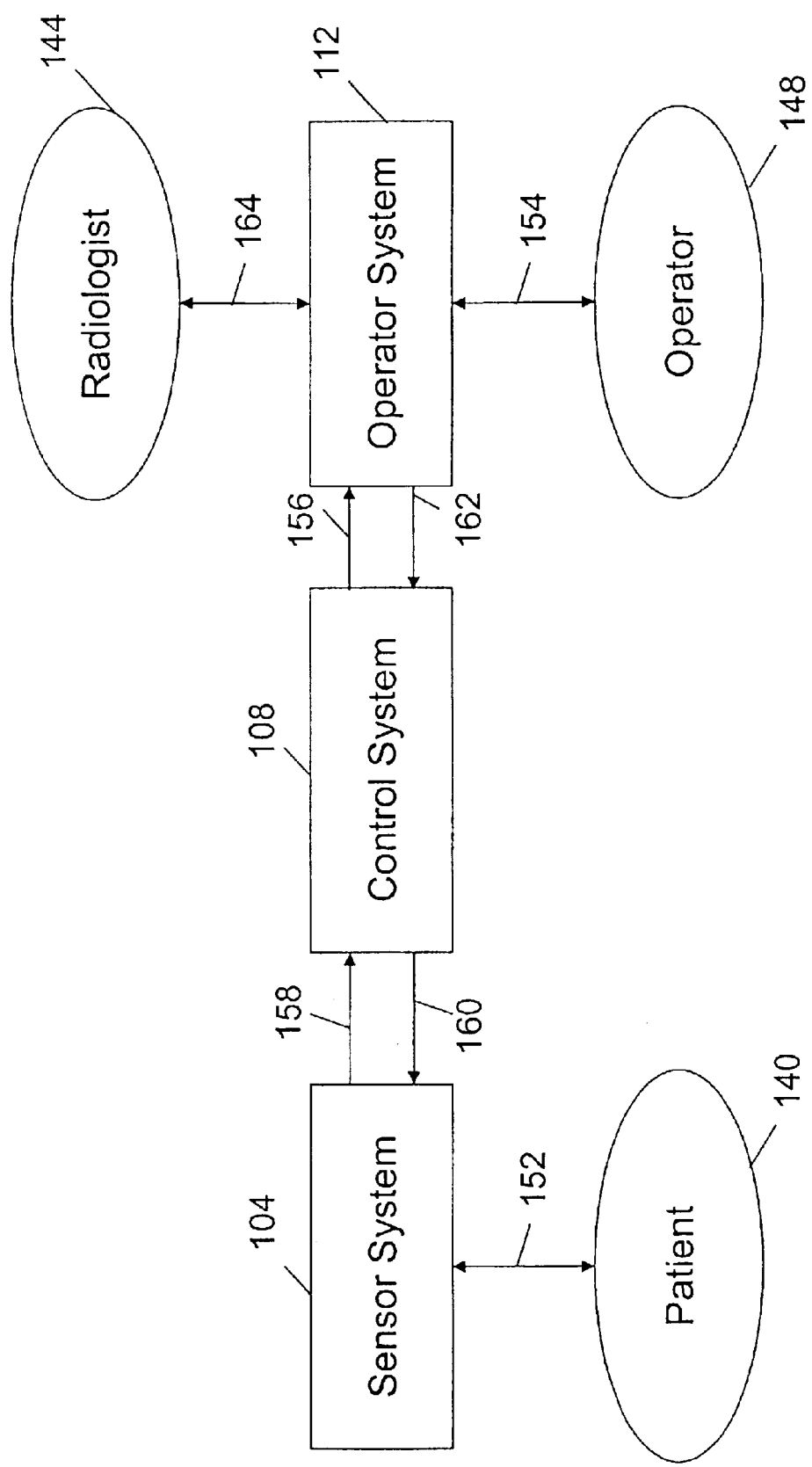

Embodiments of the invention are directed generally to a method and apparatus for examining an object under study, such as tissue. FIGS. 1A and 1B provides a general structural overview of a system that may be configured according to an embodiment of the invention appropriate for medical applications, particularly for ultrasound imaging of a patient's breast. While FIG. 1A shows the physical arrangement of the system components, FIG. 1B shows the logical interconnection of those components and how individuals interact with the system.

The system includes a sensor system 104, a control system 108, and an operator system 112. Each of these systems is described in greater detail below. A connection 116 is provided for the transfer of information between the sensor system 104 and the control system 108 and a connection (not shown in FIG. 1A) is provided for the transfer of information between the control system 108 and the operator system 112. In some embodiments, such connections may comprise, for example, ethernet connections.

In the embodiment shown, the sensor system 104 includes a support 136, a source for power connections 120, and a sensor that includes a pair of paddles 128. The lower paddle 128-2 is fixed to the support 136, but the upper paddle 128-1 is configured to be moved with handle 132 to compress the patient's breast between the two paddles 128. While the illustrated configuration of parallel paddles is especially suitable for examination of breast tissue, other paddle configurations may be used for the examination of other tissues. For example, in one embodiment, the paddles are oriented orthogonally; such an orientation is especially suitable, for example, for examination of the pancreas. In other embodiments, still other intermediate orientations of the paddles may be used. Each of the paddles 128 comprises arrays of ultrasonic transmission and receiving elements ("transducers"). In one embodiment, 512 transmission elements and 512 receiving elements are provided in each paddle. A tomographic "view" is defined by data generated for transmission of acoustic radiation from a single transmission element and reception by a plurality of the receiving elements. A tomographic "slice" is defined by data generated for a plurality of views, i.e. derived from transmission of acoustic radiation from a plurality of transmission elements and reception by a plurality of receiving elements.

The control system 108 comprises hardware used to form and time ultrasonic transmission pulses. It further comprises circuitry that records the received ultrasonic waveforms. In one embodiment, the control system 108 is partitioned into a plurality of receiver cards that each comprise a plurality of channels. In one embodiment, 64 receiver cards are provided, each comprising 16 channels. A receive waveform from each channel is amplified and digitized with a high-dynamic-range analog-to-digital converter ("ADC"). After each transmission pulse, the waveform data are compressed and transferred to a local random-access memory ("RAM") capable of storing the waveform data for at least 100 tomographic slices. Such an architecture permits recordation of a tomographic slice in approximately 0.3 seconds so that the total acquisition time for a 100-slice breast scan is approximately 30 seconds.

Thus, in operation, the patient 140 has an interaction 152 with the sensor system 104 by being positioned so that the paddles 128 are contacting the patient's breast. The operator 148 has an interaction 154 with the operator system 112 to set up the operational parameters. In one embodiment, the operator system 112 is configured to provide a graphical user interface from which operational parameters such as mode selection and timing initiation may be established. The operator system 112 derives control information from the instructions provided by the operator 148, which is then transferred through interaction 162 to the control system 108.

Once the operation mode has been established, data acquisition by the sensor system 104 is initiated by a master timing pulse derived from a master timing oscillator comprised by the control system 108. Such a pulse is communicated to the sensor system through interaction 160. The sensor, shown as paddles 128 in the illustrated embodiment, insonify the tissue volume and receive transmitted and reflected radiation. Transducers within the paddles 128 convert the received acoustic information into electrical signals that are communicated back to the control system 108 through interaction 158. The control system 108 performs an analysis of the electrical signals to derive image information that is returned to the operator system 112 through interaction 156. A professional evaluator 144, such as a radiologist, may then interact directly with the operator system 112 to view the rendered data. In alternative embodiments, selected views of the rendered data may be printed or stored for later viewing and analysis by the evaluator 144.

The structural overview provided in FIG. 1A resembles a current mammogram suite. Such a structure is advantageous in that it permits existing mammographic equipment to be modified to implement embodiments of the invention, requiring no additional rooms to house equipment comprised by the system within a breast center. In one embodiment, discussed in additional detail below, the paddles 128 may be clipped onto existing mammogram equipment, while in another embodiment the support 136 may be a separate free-standing structure with mechanisms to adjust and position the paddles 128. Also, while FIG. 1A shows the support 136 as a solitary unit within a room where the final interpretation is performed, the invention is not intended to be limited in this way. In particular, multiple sensor head inputs from different rooms may be used with a remote viewing station that serves as a client to a main system server may be used. The remote viewing station may be contained within a standard picture-archiving computer system ("PACS"). In embodiments where a breast center includes multiple mammography rooms, multiple sensor systems 104 may be included, each of which is wired into a central control system 108, thereby reducing the cost for additional units.

Figure 2:
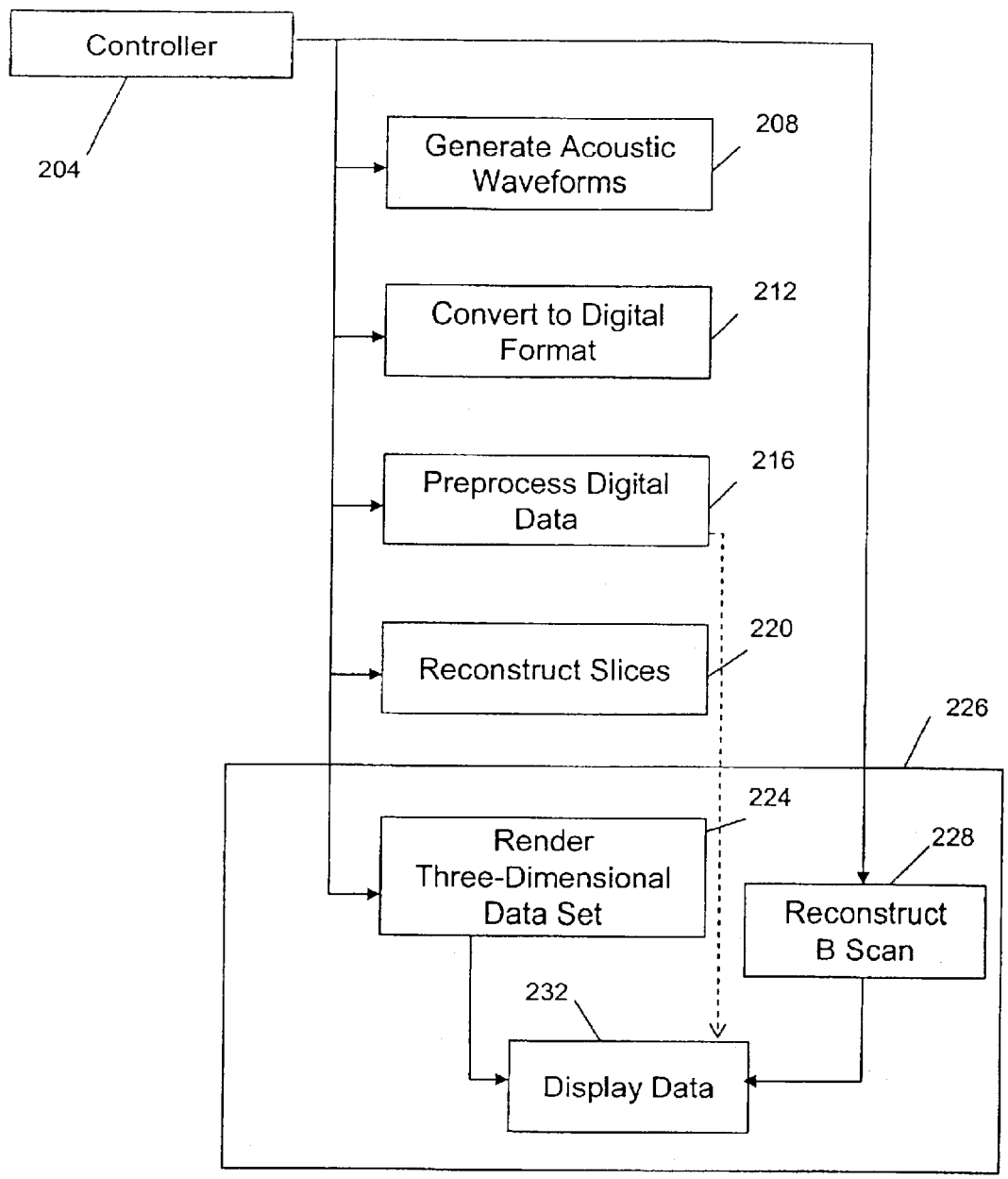
FIG. 2 provides a flow diagram providing an overview of the functional hierarchy used in an embodiment.

FIG. 2 provides a overview of the functional hierarchy of the system and indicates eight primary functions performed by the system. At block 204, a controller function is provided for the system. The controller function comprises coordinating the generation of acoustic waveforms at block 208, conversion of the waveforms to digital format at block 212, preprocessing the digital data at block 216, reconstructing B-scan images at block 228, reconstructing two-dimensional slices at block 220, rendering three-dimensional data sets at block 224, and displaying data and images at block 232. In each instance, the controller function comprises defining setup conditions for each of the other functions and determining when the function is complete.

The generation of acoustic waveforms at block 208 comprises: (1) positioning acoustic transducers for each tomographic slice; (2) generating the acoustic pulses to insonify the tissue; (3) capturing waveforms transmitted through and reflected from the tissue; and (4) using acoustic pulse timing signals to control the conversion function at block 212. The acoustic transducers are positioned by first moving them to a known home position prior to a scan cycle. The number of tomographic slices to be generated and the spacing between the slices is then received from the controller function 204. These acoustic pulses are generated by receiving transmit setup information form the controller function 204, the transmit setup information including the number and location of the transmission elements, the ganging of the transmission elements, the wave shape of the transmit pulse, and the transmit timing. Acoustic pulses are thus generated according to the setup parameters.

Once the transmitted and reflected waveforms are captured, they are processed by the conversion function at block 212. Such conversion into digital format comprises receiving both conversion setup information from the controller function 204 and receiving waveforms and timing signals from the generation function 208. In one embodiment, the minimum sampling is at least three times the highest frequency of interest, equivalent to 1.5 times the Nyquist criterion. The waveforms are converted to digital format under control of the timing signals and the digitized data are sent to the preprocessing function at block 216.

At block 216, the digitized data are preprocessed. This preprocessing comprises receiving setup information from the controller function 204 and receiving timing information from the conversion function 212. Regardless of the type of preprocessing called for by the controller function 204, the preprocessing function 216 reduces the amount of data collected by limiting the bandwidth of the data and by limiting the number of data samples. These windowed data are saved for further processing. In one embodiment, depending on the setup parameters received from the control function, preprocessing comprises determining the time of arrival and the amplitude of the direct coupling pulse; the direct coupling pulse is then removed and the remainder of the time series of data is retained, from which the complex phase and amplitude are determined for the remaining data. In certain embodiments, preprocessing further comprises sending data-quality images to the display function so that the operator 148 can assess the quality of the data being collected.

At block 220, two-dimensional tomographic slices are reconstructed. In embodiments having a plurality of sensor systems 104, each reconstruction may be coordinated by a central control system 108 rather than requiring a reconstruction system to be associated with each sensor system. Reconstructing such slices comprises receiving setup parameters and a signal to begin reconstruction from the controller function 204. Preprocessed data are received from the preprocessing function 216 and may perform any of a variety of reconstructions described in detail below. Such reconstruction algorithms include, without limitation, full-aperture tomography ("FAT") algorithms, quantitative full-aperture tomography ("QFAT") algorithms, diffraction tomography algorithms, and full-wave reconstruction algorithms. In some embodiments, a plurality of reconstruction algorithms are executed on the same data set to provide additional diagnostic information.

The two-dimensional reconstructed slices are assembled into a three-dimensional data set. In one embodiment, each element of the three-dimensional data set contains values for at least one physical quantity, such as sound speed, attenuation, density, compressibility, reflectivity, absorption, and/or acoustic impedance changes from each of the reconstructions. A three-dimensional data set is thus rendered at block 224 upon receipt of setup information from the controller function 204, with a signal to display the rendered data. In one embodiment, the rendering is capable of providing three orthogonal views of arbitrary orientation and position. In another embodiment, the rendering is capable of superimposing data derived from a plurality of reconstruction techniques. Such a plurality of reconstruction techniques permit production of isosurface or semitransparent volume rendering.

At block 228, B-scan images are reconstructed. Such reconstruction comprises receiving setup information from the control system and receiving data and timing signals from the preprocessing function 216.

At block 232, data are displayed in the form of images. Rendered images and B-scan images are received from the rendering function 224 and from the B-scan reconstruction function and displayed for the operator 148. In certain embodiments, data-quality images derived from the preprocessing function 216 are also displayed so that the operator 148 may assess the quality of the data being collected.

In FIG. 2, block 226 is used to indicate functions that may advantageously be performed within a PACS system, including rendering the three-dimensional data set 224, reconstructing a B-scan image 228, and displaying the data 232. Assignment of such functions to a PACS system in especially useful for a clinic setting having a plurality of sensor systems 104 by limiting the cost and complexity of the operator system 112. For example, in an embodiment, reconstruction tasks could by limited to a current patient, with the operating system 112 needing only to display sufficient data for a technician to verify that adequate data had been gathered on the current patient to complete the exam. By having modularized sensor collection, but centralized rendering and reconstruction, more practical systems for larger clinic centers are enabled. Data may then branch out from the centralized control system to multiple physician viewing stations, enabling modularized interpretation.

2. Sensor System

The sensor system used in embodiments of the invention comprises ultrasonic transmission and receiving elements, and a mechanism for transferring both transmitted and received acoustic energy to the tissue being studied. One embodiment, shown explicitly in FIGS. 3A–3C, uses a pair of acoustic paddles 128. Such a paddle arrangement has the advantage when used with breast imaging of leaving a portion of the breast exposed to perform biopsy extractions. Such biopsy extractions may be performed in response to data previously acquired, or the imaging system may instead be used to provide real-time guidance for performing a very accurate biopsy. In addition, specific embodiments described below use a geometry that is particularly effective at insonifying the axilla region and tissues near the chest wall. Such regions are important sites for breast cancer detection, but are not as well examined by using, for example, a circular array geometry.

Figure 3B:
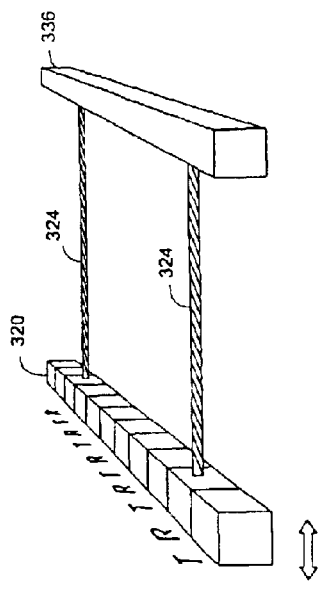
FIG. 3B provides a perspective view of acoustic arrays that may be used within the paddle arrangement.
Figure 3C:
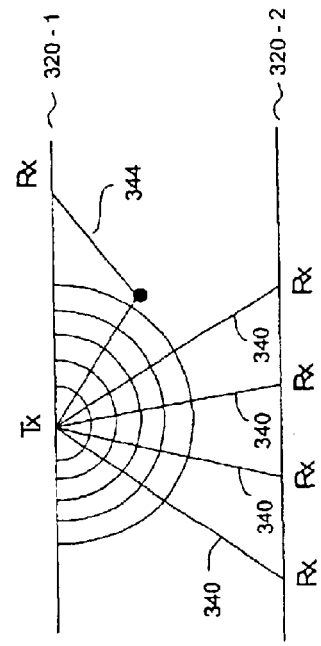
FIG. 3C provides a schematic illustration of how waves are propagated within the paddle arrangement between transmission and receiving elements.
Figure 3A:
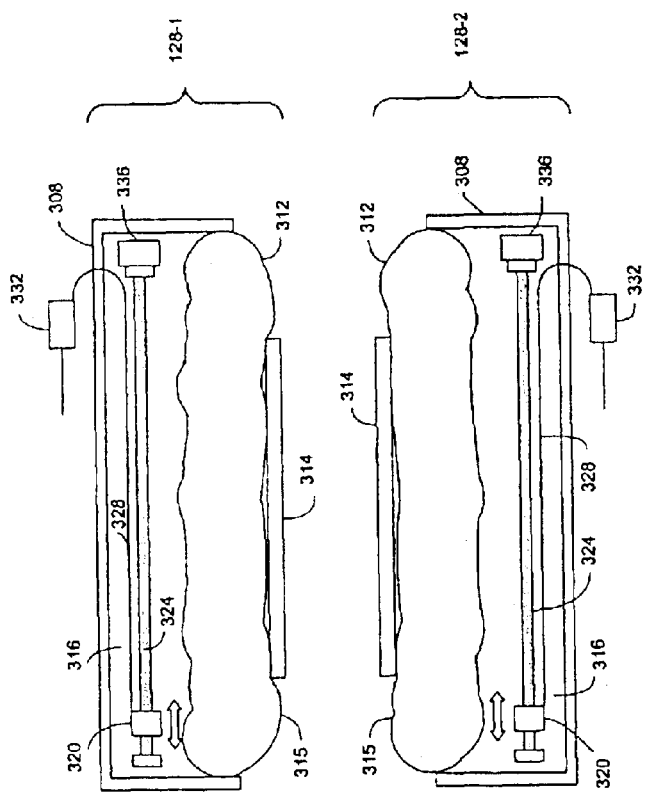
FIG. 3A provides a cross-sectional view of a paddle arrangement used for insonification of tissue.

FIG. 3A shows a cross-sectional view of both the upper 128-1 and lower paddles 128-2 in one embodiment. Each of the acoustic paddles 128 comprises an enclosure 308 and a pliable coupling bladder 312. The enclosure 308 comprises an acoustic transmission medium 316. In one embodiment, the enclosure 308 further comprises an acoustic-energy absorbing material to reduce unwanted reflections when the sensor system is in operation.

The pliable coupling bladder 312 is filled with a medium that is acoustically matched to the transmission medium 316. In operation, the exterior portion of the coupling bladder 312, i.e. that portion that is to be in contact with a patient's tissue, is coated with a coupling gel. The quality of data generated may be adversely affected by the presence of bubbles when the paddle is placed in contact with the tissue. The pliability of the coupling bladder 312 thus provides an adaptable interface for improving patient contact and reducing trapped air bubbles. In some instances, only a portion of the coupling bladder 312 is pliable, depending on characteristics of the tissue to be studied, particularly the firmness of the tissue to be studied. Patient scanning follows an approximately inverse law of firmness in relation to the surface being scanned. For example, imaging of a soft organ such as the breast benefits from a firmer flat surface to squeeze out bubbles during mild initial compression. Conversely, imaging of firm and/or irregular contours such as a joint surface benefits from greater pliability. A coupling bladder 312 that includes both firm portions 314 and pliable portions 315 may thus effectively accommodate specific tissue configurations. For example, the coupling bladder 312 for use in breast examination may be pliable on the portion of the paddle 128 extending into the firmer tissues of the axilla, with the remainder of the paddle 128 being flat and firm to better squeeze out air bubbles in contact with the compliant breast tissue. The resultant ability to facilitate insonification of the axilla region is beneficial because it permits acoustic coupling of regions that are traditionally difficult to reach.

Within the transmission medium 316 of each paddle is included a transducer array 320. In a particular embodiment, the array 320 is configured as a monolithic linear assembly that extends orthogonally to the cross section shown in FIG. 3A. In one embodiment, the array 320 is configured as part of a carriage subsystem for moving the array 320 in an orthogonal direction, i.e. left-right in FIG. 3A. Such movement permits the array 320 to scan through the tissue to be examined. Thus, in addition to the array 320, the carriage subsystem comprises translation elements, such as a lead screw arrangement 324 and mount 336. Other translation mechanisms, such as use of a recirculating ball, will be known to those of skill in the art and may be substituted for the illustrated arrangement. In alternative embodiments, the scanning capability may be achieved electronically rather than mechanically. In particular, the mechanical scanning may be mimicked by using capacitive micromachined ultrasonic transducers ("CMUT") or equivalent solid-state elements under electronic control.

A detail of the transducer array 320 and translation mechanism is shown in FIG. 3B. In one embodiment, each array 320 includes 512 transmitting elements ("T") and 512 receiving elements ("R"). In some embodiments, the spacing ("pitch") between the receiver elements R is set substantially equal to one half wavelength for the average speed of sound in the appropriate tissue in order to satisfy the spatial Nyquist criterion, although experimentation by the inventors has established that high-quality data may be obtained with necessarily meeting the Nyquist criterion. Embodiments in which the Nyquist criterion is not met permit data to be collected with fewer transmitting and receiving elements, which may be preferred in order to reduce the cost of supplying the elements and reducing the amount of data to be analyzed. The inventors have found that particularly good results may be achieved without meeting the Nyquist criterion at lower frequencies. It is believed that this results from a synergistic combination of preprocessing, focusing, and other process steps.

In a specific embodiment where the tissue to be imaged comprises breast tissue, the pitch between receiver elements for a center frequency of 2 MHz is approximately 0.385 mm. The transmitting elements T are generally placed at the same pitch as the receiver elements R. This may be readily accomplished in an embodiment where the transducer array 320 comprises a linear array of alternating transmitting T and receiving elements T. In one embodiment, the dimensions of both transmitting T and receiving elements R is about 0.19×6 mm$^2$.

The translation mechanisms of the two acoustic arrays in the upper 128-1 and lower paddles 128-2 are configured so that the arrays are positioned substantially opposite each other in the same acoustic plane with the opposing elements facing each other. Thus, in a specific embodiment, each of the (say) 1024 transmitting elements T sends, in turn, a 2 MHz, three-cycle pulse. The acoustic waveform from each transmitted pulse is received by all (say) 1024 receiving elements R. In such a specific embodiment, the time between transmit pulses is approximately 300 $\mu$s. The time to acquire a tomographic slice of data is thus 0.307 seconds (300 $\mu$s per pulse time 1024 pulses). This is shown schematically in FIG. 3C, in which a single transmit pulse $T_x$ results in a plurality of received signals $R_x$.

The transmitting and receiving elements may be configured differently in various embodiments. Generally, because of the need to convert between acoustic and electrical signals in the system, the transmitting and receiving elements will comprise a piezoelectric or giant-electrostriction ferroelectric material. A piezoelectric material, such as poly (vinylidene fluoride) ("PVDF") deforms in response to applied electric potential. As a result, application of a periodic potential causes periodic deformation of a piezoelectric so that it emits acoustic waves as a transmitter T. Similarly, the piezoelectric may be used as a receiver R since its periodic deformation by an acoustic wave will generate a periodic current. A giant-electrostriction ferroelectric material may be configured to act similarly by polling it with a large voltage while held above its Curie temperature. Examples of such materials include lead zirconate titanate ("PZT") and lithium niobate.

Both PZT and PVDF have similar sensitivity, however the PZT elements have lower impedance, making it easier to interface the PZT elements to preamplifiers. The PZT elements typically have a 2 k$\Omega$ resistive impedance at a 2 MHz resonant frequency while the PVDF elements typically have a 166 k$\Omega$ capacitive impedance at 2 MHz. The PVDF elements, however, typically have significantly smaller manufacturing costs. A further consideration is the fact that the use of PZT is currently a mature technology used by manufacturers of conventional ultrasound equipment while PVDF has typically not been used for high-frequency arrays.

In other embodiments, the transmitting and receiving elements may comprise CMUT elements. Such elements are small diaphragm-like devices with electrodes that may act as receivers by converting the sound vibrations of an acoustic signal into a modulated capacitance. They may act as transmitters by modulation of the capacitive charge to vibrate the diaphragm of the elements and thereby transmit an acoustic wave. Such CMUT elements are manufactured using semiconductor processes and have dimensions in the range of 10–200 $\mu$m, although larger elements may be formed by grouping a plurality of CMUT elements together for operation in unison as a single transducer element. Further details regarding the fabrication and operation of CMUT elements is described in U.S. Pat. No. 6,443,901, entitled "CAPACITIVE MICROMACHINED ULTRASONIC TRANSDUCERS," issued Sep. 3, 2002, the entire disclosure of which is herein incorporated by reference for all purposes.

Some of the received signals, denoted by rays 340 in FIG. 3C, correspond to transmission through the tissue so that they are received by a receiving element R on a different acoustic array 128 than the transmission element T. Some of the received signals, denoted by ray 344, correspond instead to reflection from the tissue so that they are received by a receiving element R on the same acoustic array 128 as the transmission element T. For the physical arrangement shown, cylindrically or spherically shaped wave fronts emanating from each transmitting element T provide sufficient angular diversity to achieve the required resolution of the tomographic reconstructions described below.

For such a configuration, the beam pattern produced for each slice is wide in an image plane but is narrow in a thickness plane. An analysis for a 0.375-mm-wide array element indicates that the in-plane beam width is greater than 100°. Thus, once a slice has been taken, both acoustic arrays 128 are moved a distance through the thickness plane, which in one embodiment is approximately 2 mm, and the cycle is repeated. If the time allocated to move the pair of arrays is approximately 0.1 seconds, the time to take 100 slices is about 40 seconds (0.307 second per slice plus 0.1 seconds per interstice movement, all multiplied by 100 slices).

While such a method of operation is suitable for normal tomographic scans, the system is also amenable to alternative scanning techniques. For example, for B scans, a group of transmission elements T may be activated simultaneously to form a plane wave across the tissue rather than forming a series of acoustic pulses.

Figure 3D:
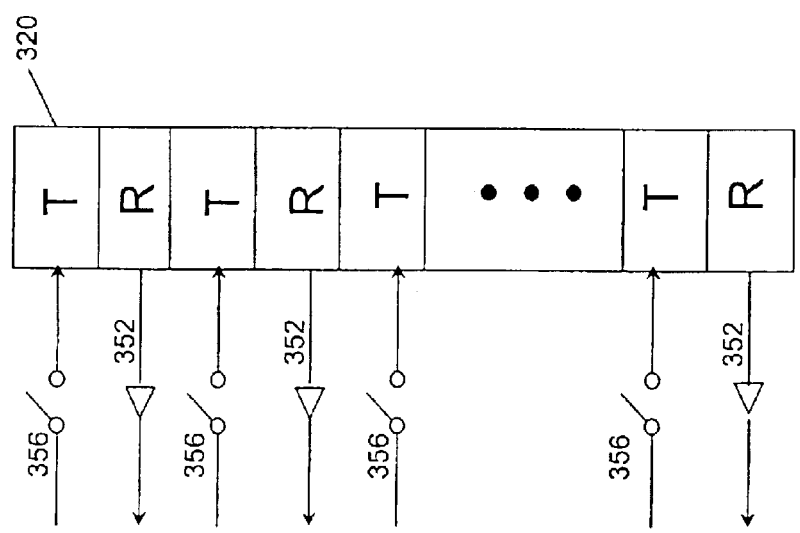
FIG. 3D provides a schematic illustration of the electrical connection with the acoustic array.

In addition to the transducer array 320 and translation mechanism in FIG. 3A, the carriage subsystem may include buffer electronics for controlling the acoustic arrays 320. In one embodiment, the buffer electronics are mounted on a stable circuit board. Leads to each element of the array 320 are available at the mounting surface of the array 320. Electrical connection is provided to each array 320 through cable 316, which is connected externally with a connector 332. The head electronics for the arrays 320 is shown in FIG. 3D. The buffer electronics provide signal amplification and mounting stability for the acoustic array. Each receiving element R is electrically connected with a buffer amplifier 352. The buffer electronics also provides a termination point for signal lines to a drive electronics element 360, described below. FIG. 3D also shows switches 356 used for individual activation of the transmission elements T. In one embodiment, the ultrasonic elements generate signals in the receive mode in a range from about 10 $\mu$V–1 V. At low signal levels, the signal/noise ratio of the elements may thus degrade rapidly as a result of cable losses. This may be compensated for by additionally including a low-noise amplifier in close proximity for the receiving elements R so that small feasible signals are still detected.

Figure 3E:
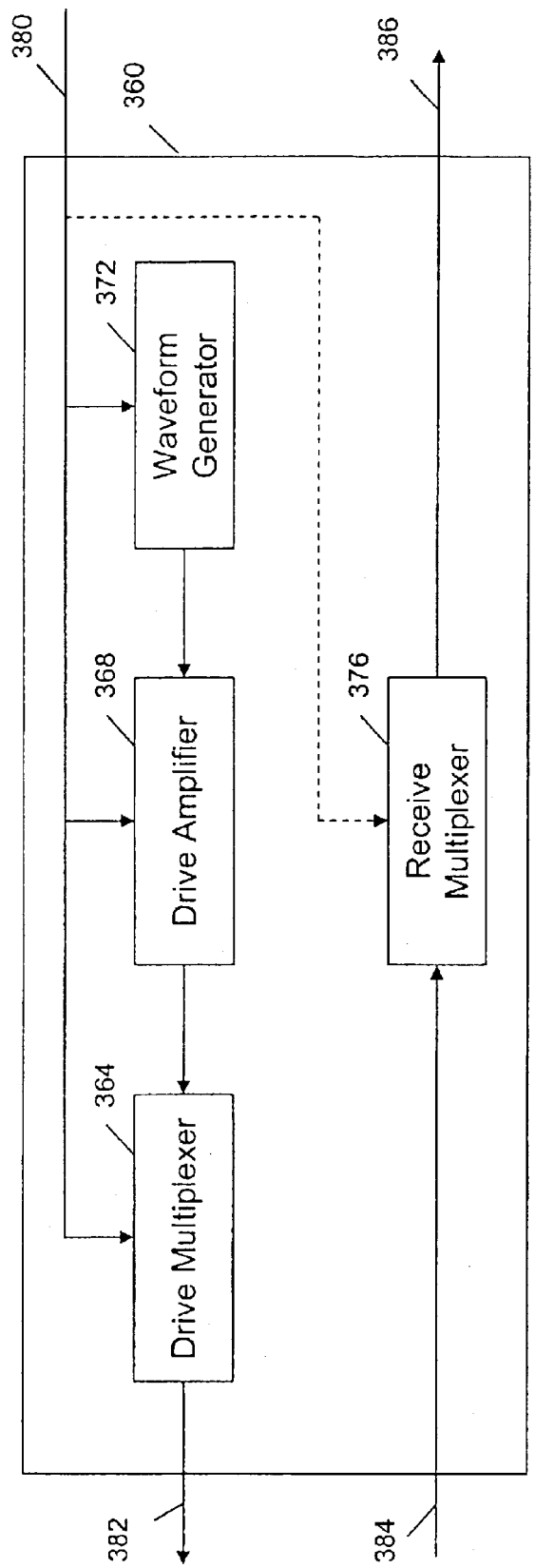
FIG. 3E provides a schematic illustration of an electronic arrangement used to drive the acoustic arrays.

The connector 332 provides a connection between the individual buffer electronics through the cable 328 with the drive electronics element 360, shown schematically in FIG. 3E. The drive electronics element 360 comprises a drive multiplexer 364, a drive amplifier 368, and a waveform generator 372. It may additionally comprise a receive multiplexer 376 in certain embodiments. The drive electronics element 360 may be mounted on the sensor system support 136 in a manner that minimizes the physical distance between the drive amplifier 368 and the acoustic array 320.

The waveform generator 372 is programmed from a timing and control element 404, described below with respect to the control system 108. Signals from the timing and control element 404 are received by elements of the drive electronics element 360 through interaction 160, which connects the control system 108 to the sensor system 104. Once the waveform generator 372 is programmed, the waveform is sent to the drive amplifier 368 upon receipt of a master trigger signal 380 from the timing and control element 404. The drive amplifier 368 takes the analog waveform generated by the waveform generator 372 and amplifies the signal to a large peak-to-peak voltage. In one embodiment, this peak-to-peak voltage is approximately 100 V. The amplified signal is then transmitted to the drive multiplexer 364. The drive amplifier 368 is gated on and off by signals 380 from the timing and control element 404. In one embodiment, the drive amplifier drives between 1 and 128 transmission elements T. The duty cycle for the amplifier is generally less than 4%, corresponding to a 10-$\mu$s transmit pulse every 300 $\mu$s. The drive multiplexer transmits the drive signal 382 to the acoustic array 320.

In some embodiments, a receive multiplexer 376 is provided. Signals 384 from the receiving elements R are multiplexed and transmitted to the control system 108 for analysis with multiplexed signal 386. The multiplexed signal 386 is communicated to the control system 108 through interaction 158, which connects the sensor system 104 to the control system 108. Such a receive multiplexing element may be preferred in embodiments that achieve acceptable image-reconstruction results with a smaller number of transmit views. For example, if acceptable results may be derived from 128 transmit views, a set of 8:1 multiplexers will greatly reduce hardware costs. The receive multiplexer 376 will generally not be used in embodiments that use the full number of possible transmit views, since multiplexing of receive lines for 1024 transmitters sending pulses every 300 $\mu$s is inconsistent with the desire to maintain a short patient examination time.

Certain aspects of the paddle arrangement are similar to physical arrangements currently used in mammographic studies. For example, the paddles described above may be clipped onto existing mammography equipment, such as by using the film cassette slot of an existing mammography unit as an anchor for the lower paddle while replacing the upper mammography compression paddle with the upper paddle described above. The specific attachments and fittings to accomplish such a conversion may depend on the specific arrangements of the compression paddles of current mammography-equipment manufacturers. Thus, in one embodiment of the invention, the paddle arrangement is configured simultaneously with the ultrasound transducers described above and with x-ray emitters and sensors configured according to a traditional mammography arrangement. The x-ray sensors typically comprise chemical-based x-ray-sensitive photographic films. As described below in Section 6, such an arrangement permits the simultaneous collection of x-ray mammographic data and ultrasound data, which may be analyzed in concert to provide additional information beyond either type of data alone.

3. Control System

Figure 4A:
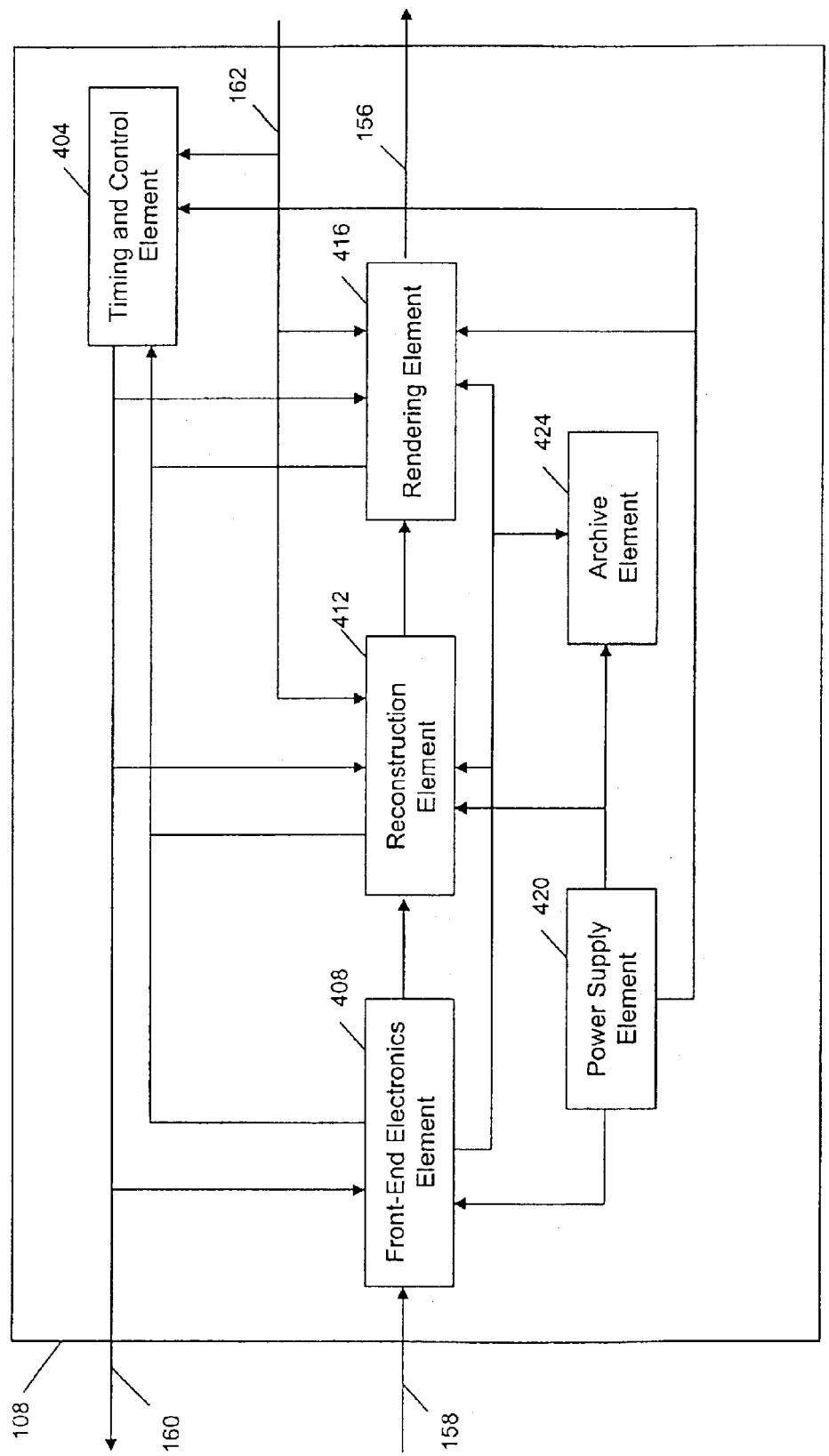
FIG. 4A provides a schematic illustration of an control system used to operate aspects of the system.

An overview of the control system 108 is provided in FIG. 4A. The control system 108 comprises the timing and control element 404, a front-end electronics element 408, a reconstruction element 412, a rendering element 416, an archive element 424, and a power supply element 420. The power supply element 420 is configured to supply power to the active elements of the control system 108, using standard 115 V alternating current in one embodiment. Signals are provided to the control system 108 from the sensor system 104 through interaction 158 and from the operator system 112 through interaction 162. Signals are provided by the control system 108 to the sensor system 104 through interaction 160 and to the operator system through interaction 156.

The timing and control element 404 receives setup parameters from a controller element 516 comprised by the operator system 112 and performs a variety of timing functions to control operation of the control system 108. For example, a master timing signal generated by the timing and control element 404 controls the front-end electronics element 408, the reconstruction element 412, and the rendering element 416. In addition, the master timing signal is used by various elements of the sensor system as described above to achieve general synchronization of the entire system operation. The master timing signal is derived from a master timing oscillator comprised by the timing and control element 404 and all timing functions may be referenced to this oscillator.

Figure 4B:
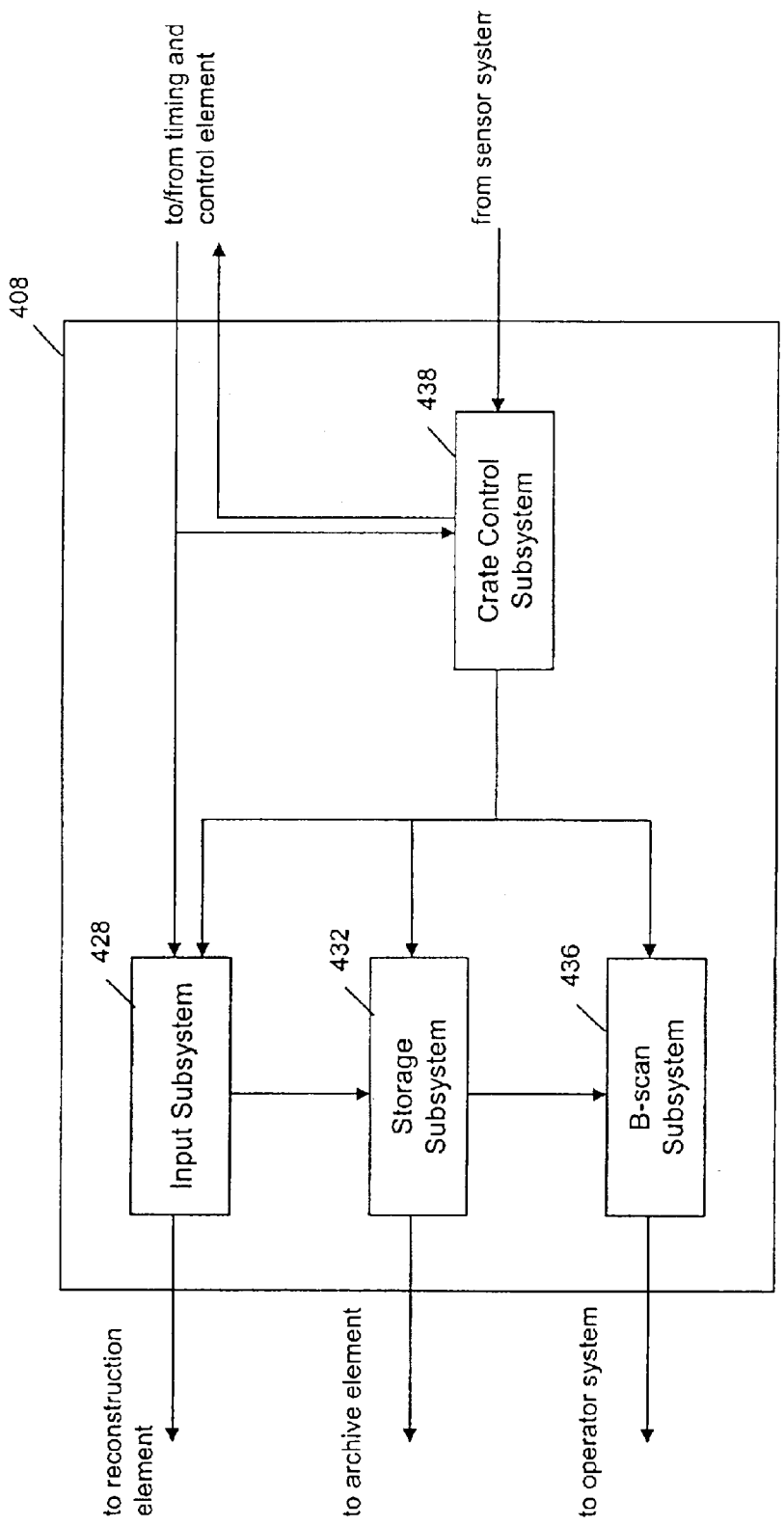
FIG. 4B provides a schematic illustration of a front-end electronics element used in one embodiment.

Additional detail illustrating the front-end electronics element 408 is shown schematically in FIG. 4B for an embodiment that conforms to the versa modular European ("VME") standard. In this embodiment, the master timing signal from the timing and control element 404 is provided both to an input subsystem 428 and to a crate control subsystem 438. These subsystems interact as described below with a storage subsystem 432 and a B-scan subsystem 436. For purposes of illustration, the discussion below refers to an embodiment in which 1024 transmission and receiving elements are addressed; it will be evident to those of skill in the art that modifications may readily be made to adapt the arrangement to different number of transmission and receiving elements. In alternative embodiments, a different bus technology may be substituted for VME. One alternative comprises a compact peripheral component interconnect ("CPCI"), which is generally less expensive to implement than the VME configuration. The storage subsystem 432 may have the ability to transfer and/or add archive elements, a feature that is useful in embodiments where a PACS system is used to achieve modularized sensor collection, as described above.

Figure 4C:
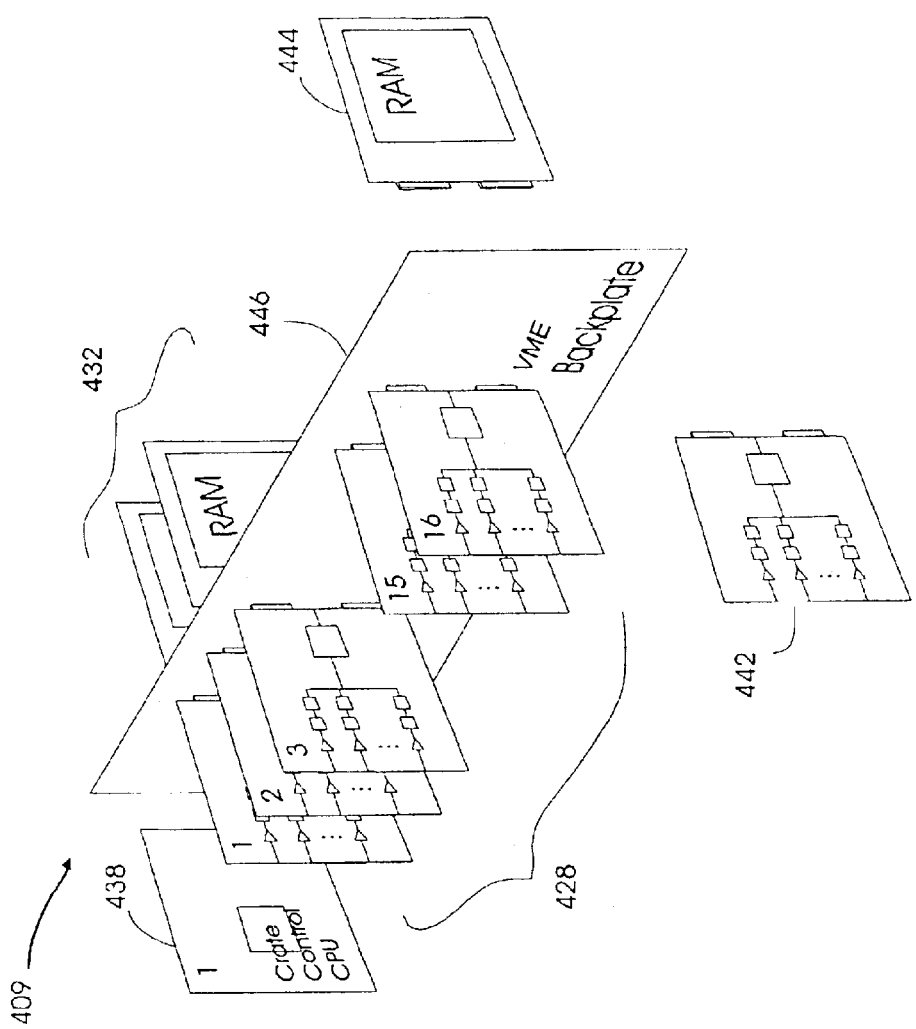
FIG. 4C provides a perspective view of a VME embodiment of the front-end electronics element.

A physical structure for the front-end electronics element 408 is illustrated in FIG. 4C. A suitable VME interface crate 409 for use with the front-end electronics comprises a plurality of VME cards 442, a plurality of high-density random-access memory ("RAM") cards 444, and a crate control CPU card 438 connected with a VME backplate 446. A multiconductor cable assembly having at least 1024 shielded wires transmits received signals from head electronics to signal-processing electronics. The receive signals are segmented in groups of 16 channels. Each 16-channel group is connected to a VME card 442 that amplifies and digitizes the signals so that they may be processed with some form of programmable array logic, such as provided by a field-programmable gate array ("FPGA") digital-signal processor ("DSP"). Data conditioning includes detection of the amplitude and arrival time of specific ultrasonic pulses, detection of the amplitude and phase of the frequency components of each pulse, and archival of the received waveform for subsequent reconstruction. Each of the 16-channel VME cards 442 is associated with one of the high-density RAM cards 444 for archival of the waveforms for multiple tomographic slices. In an embodiment that uses 1000 data samples per waveform for 100 tomographic slices, RAM cards 444 that hold at least 3.3 Gbytes are sufficient.

Figure 4D:
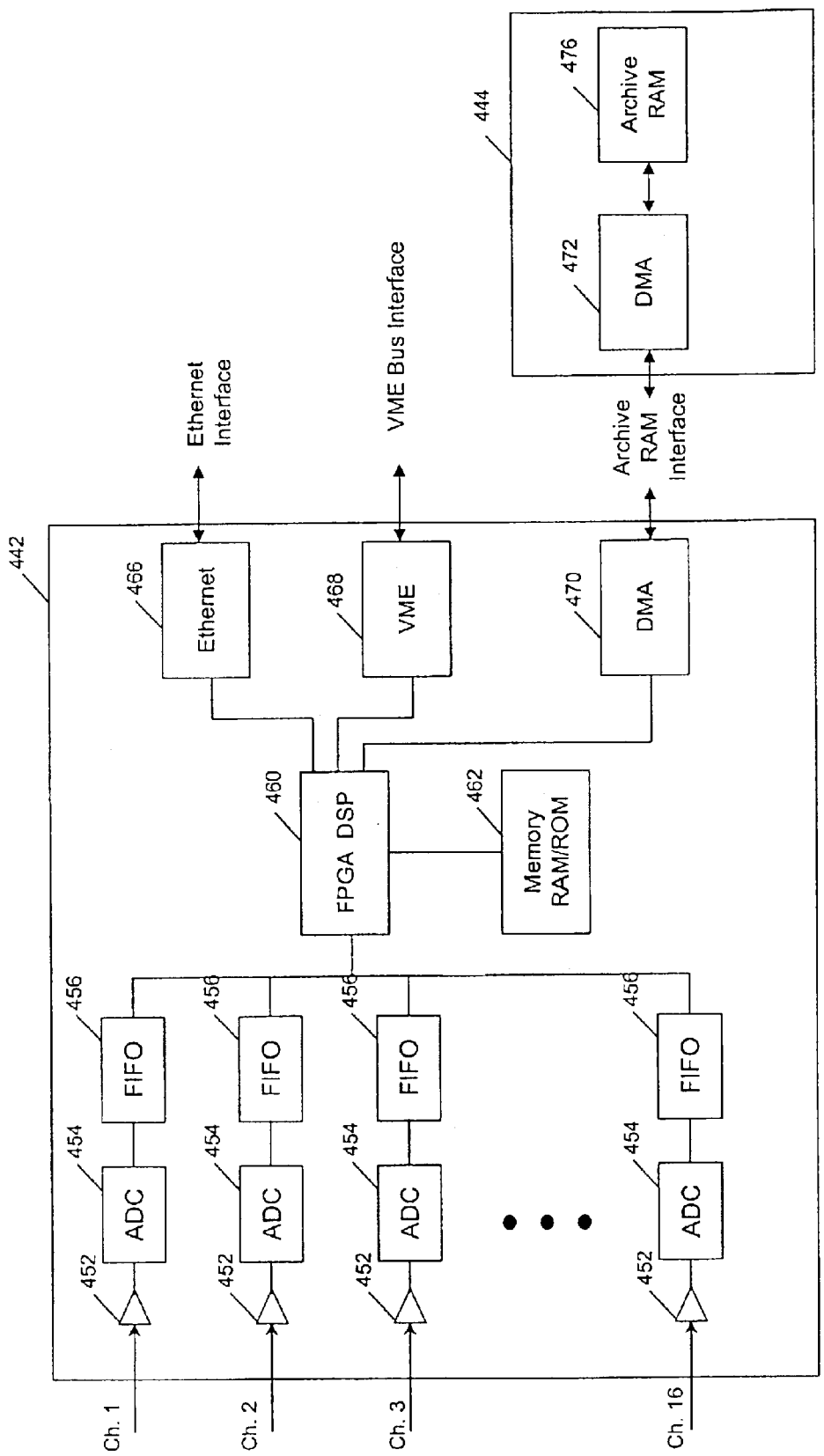
FIG. 4D provides a detailed schematic view of a particular VME card and associated RAM card in one embodiment.

A detail of the interaction between a particular VME card 442 and its associated RAM card 444 is shown in FIG. 4D.

The function of the input subsystem 428 comprised by the set of VME cards 442 is to preprocess incoming analog data. Thus, for each of 16 analog signal lines to the VME card 442, the signal is first amplified with amplifier 452. The amplified signal is then digitized with analog-to-digital ("ADC") converter 454. The digitized signal is stored in a first-in-first-out ("FIFO") memory 456. The signals stored in the plurality of FIFO memories 456 is then transferred to the FPGA DSP where at least one of two classes of image-reconstruction preprocessing is performed. Such preprocessing may use memory 462 available on the VME card 442.

One class of preprocessing comprises time-series preprocessing. The raw signal digitized from a single receiver defines the acoustic time series for a particular transmitter-receiver pair. The "direct coupling pulse" is defined as the acoustic signal that traverses the most direct route from that transmitter to that receiver. Consequently, there can be no physical information available in the signal at a time before the arrival of the direct coupling pulse at the receiver. Since all scattering information occurs after arrival of the direct coupling pulse, the digitized waveforms are windowed to extract only data following the direct coupling pulse. This may be accomplished by analog filtering and digitization to accommodate the entire dynamic range of the signal. The transmitted pulse is then be sharpened with a deconvolution method to produce a more impulse-like coupling pulse and provide improved definition of the scattered signals. This deconvolved signal, without the direct coupling pulse, is subsequently used by the reconstruction method. Examples of reconstruction methods that use time-series data include B-scan reconstruction and FAT reconstruction.

The second class of preprocessing comprises frequency-series preprocessing. In this class, the data acquisition step may be the same as described above. Following digitization, the data are transformed into a frequency domain with a Fourier-transform technique. The preprocessing method may thus derive complex frequency-domain coefficients. In one embodiment, up to ten frequency values from the spectrum are transformed. The Fourier-transformed signal is subsequently used by the reconstruction method. Examples of reconstruction methods that use frequency-series data include diffraction tomography and full-wave methods.

The storage subsystem 432, which in the illustrated embodiment comprises the plurality of RAM cards 444, accepts the waveform and/or frequency-coefficient data from the input subsystem 428 for storage. As shown in FIG. 4D, this may be accomplished using direct-memory access ("DMA") modules 470 and 472 to store the data in the archive RAM 476. Generally, each storage subsystem RAM card 444 is capable of storing all data from one input subsystem VME card 442 for data collected for one breast. During the time that the system is being reconfigured to collect data for another breast, the storage subsystem 432 transfers data to the archive element 424 over a high-speed link and/or sends the data to the reconstruction element 412.

In addition to a DMA module 470, the VME card 442 may comprise an ethernet module 466 and/or a VME bus interface module 468. Such modules may be used respectively to transfer information among other parts of the system and to provide access to the crate control CPU 438 described below.

The front-end electronics system 408 may also comprise a B-scan subsystem 436 configured to receive data from the storage subsystem 432. Such received data is used to produce real-time two-dimensional B-scan reconstructions while the input subsystem 428 is receiving further data. Methods for generating B-scan reconstructions from the time-series data are known to those of skill in the art. The reconstructed B-scan slice images are sent to the operator system 112 for real-time display.

Each of the input subsystem 428, the storage subsystem 432, and the B-scan subsystem 436 is controlled by a crate control subsystem 438, which comprises a VME controller that receives setup information from the timing and control element 404. Each VME interface crate 409 includes a crate control CPU 438 in the first slot. This crate control CPU 438 is configured to arbitrate access to the VME bus to prevent data collisions. One advantage of configuring the system with a VME architecture is that it has reliable bus arbitration and the ability for many cards containing independent CPU's to coexist in a single crate with minimal system malfunctions. In an embodiment where multiple sensor systems 104 are included in a single clinic center, the crate control subsystem 438 may be configured to provide modular control of the individual sensor systems 104. For example, data collisions from the multiple sensor systems 104 may be prevented by sequencing computer availability with the crate control subsystem 438.

Figure 4E:
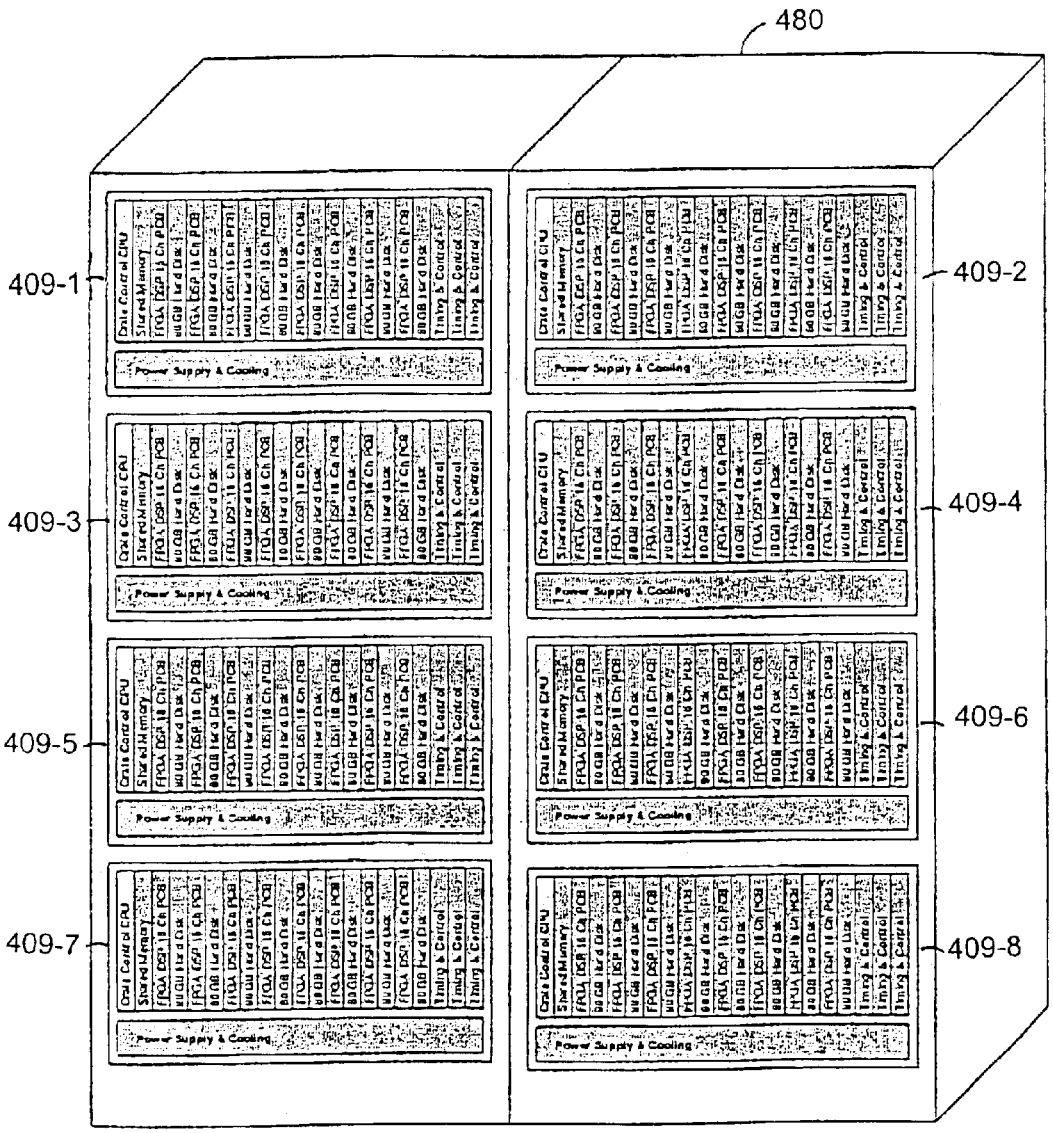
FIG. 4E provides an illustration of a rack housing that may be used to house a plurality of VME interface crates in one embodiment.

FIG. 4E illustrates that a rack housing 480 may be used to house a plurality of VME interface crates 409 configured as described above. Typically, the rack housing 480 comprises a power supply, support, and cooling for the elements within the front-end electronics element 408.

In addition to the power supply element 420, the timing and control element 404, and the front-end electronics element 408, the control system 108 may comprise additional elements. For example, the reconstruction element 412 receives setup information from the operator system 112 and performs slice reconstructions on data received from the storage subsystem 432. A variety of reconstruction methods may be used by the reconstruction element 412, some of which are described in detail below. Irrespective of the method used, reconstructed two-dimensional slices are then passed to the rendering element 416 for three-dimensional rendering. In one embodiment, the data provided to the rendering element are pixelized in a format similar to that used by other imaging modalities, such as x-ray, CT, and MRI scans, so that commercial graphics display hardware and software is used to render the data. Finally, the archive element 424 may be provided for the storage of data. When such data is to be analyzed, the system may then transfer the data to the reconstruction element 412 for eventual display by the rendering element 416.

4. Operator System

Figure 5:
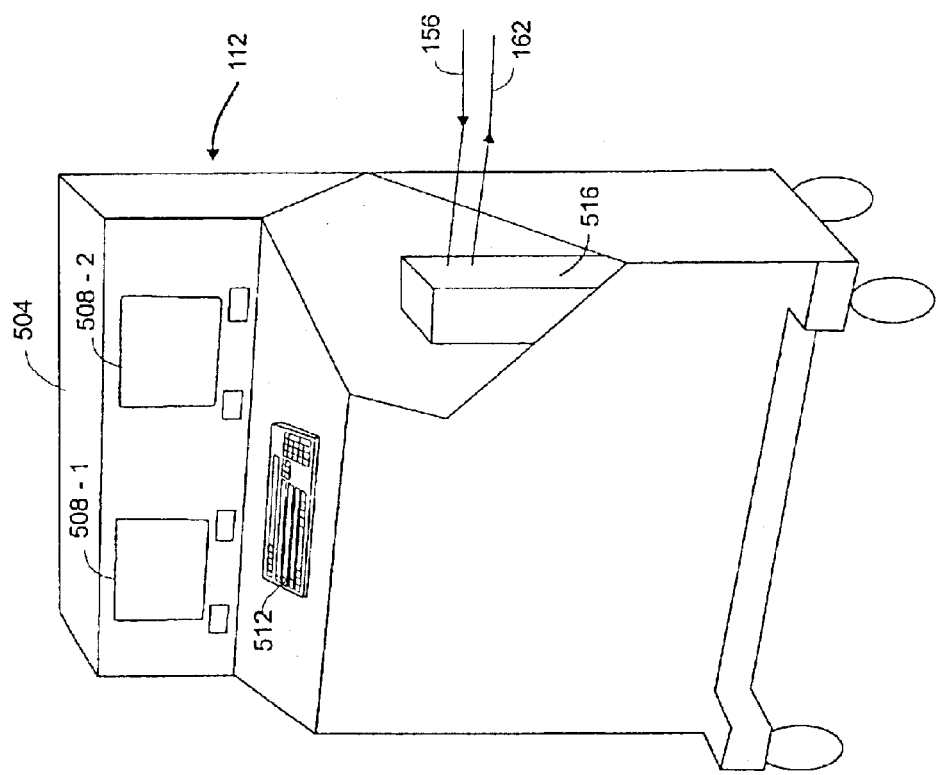
FIG. 5 is a perspective illustration of an operator system used with embodiments of the invention.

FIG. 5 provides a schematic view of one embodiment of the operator system 112. Active elements of the operator system are supported by a structural element 504, which may be configured for mobility or may be stationary in different embodiments. The structural element supports one or more display elements 508, which are shown in the illustrated embodiment as CRT screens. In one embodiment, two such screens are provided, one of which is configured to display data quality images and control screens and one of which is configured to display rendered data.

The structural element 504 also supports one or more input elements 512. The input elements may comprise a variety of devices configured for data entry, such as a keyboard with integrated track ball, a mouse, light pen, touch-panel overlays on the display elements 508, etc.

The structural element 504 also houses a controller element 516, which is configured to receive image data from the control system 108 through interaction 156 and to return information to the control system 108 as described above through interaction 162. The controller element 516 coordinates a display of images with the display elements 508 and interprets operator input derived from the input elements 512 before sending the operator commands to the control system 108. The hardware for the controller element 516 may thus comprise a general-purpose workstation processor capable of supporting dual monitors.

5. Reconstruction Methods

The system described above may be used for a number of algorithms that may comprise very different input and computational requirements. While each of the algorithms may be used in certain embodiments for the production of images, the output images may represent different physical quantities. Generally, all of the methods make use of the fact that the scattering of the acoustic wave propagated through the insonified object is modified in terms of its speed, phase, amplitude, and path by features within the object. The change in waveform contains information about the acoustic characteristics that caused the change.

a. Full Aperture Tomography ("FAT")

Figure 6:
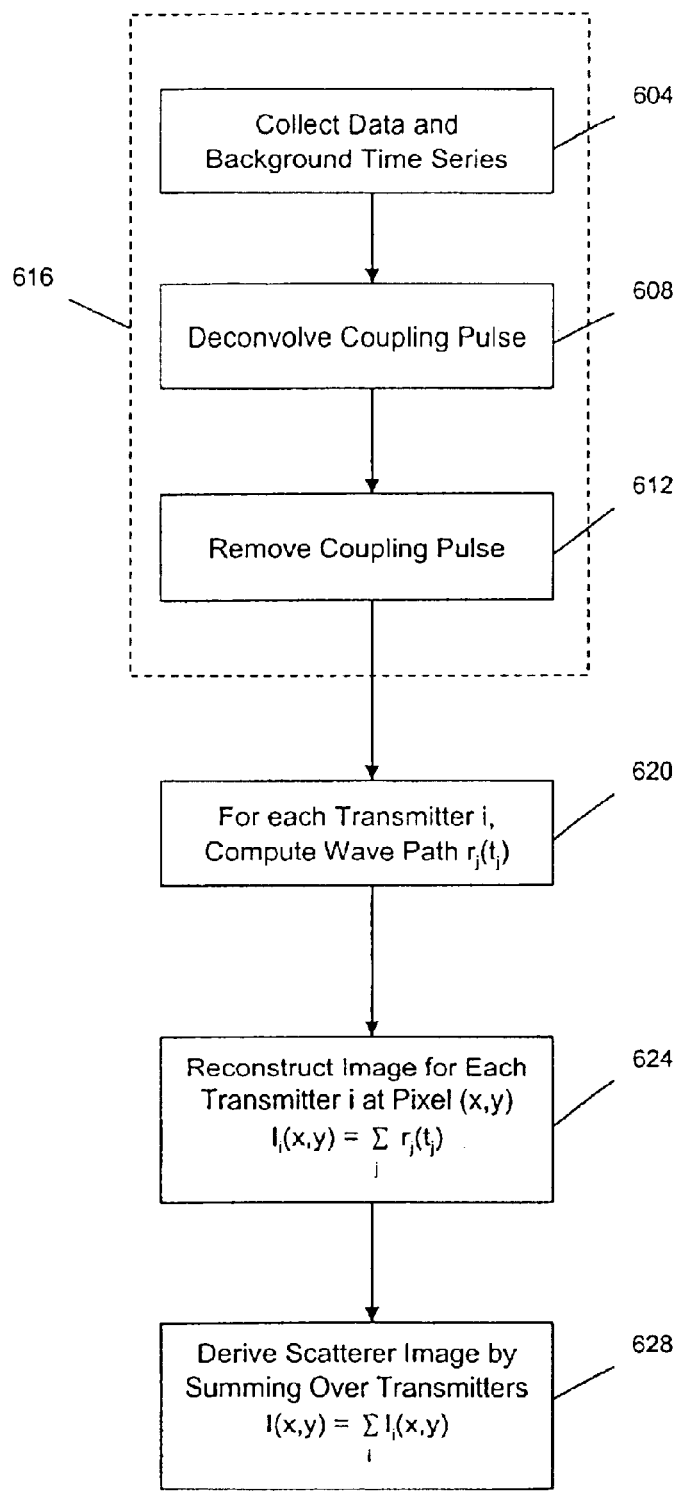
FIG. 6 is a flow diagram illustrating a full-aperture tomographic reconstruction technique.

FIG. 6 provides a flow diagram illustrating an embodiment for reconstruction that uses full-aperture tomography ("FAT"). FAT is a method that uses time-series data directly for the reconstruction and produces images that highlight scattering sources in the insonified object. The method relies on isotropic wave scattering and uses a known sound speed for the scattering medium.

Block 616 provides a portion of the method used to extract the direct coupling pulse, i.e. that acoustic signal that traverses the most direct route from transmitter to receiver for any transducer pair. This aspect of the method may be performed by the front-end electronics element 408, as described above, as part of the preprocessing function 216 discussed with respect to FIG. 2. At block 604, the data time series and background time series are collected by the sensor system 104 described above. The direct coupling pulse is deconvolved from the time series at block 608 and removed at block 612. This aspect of the method thus provides the time series data used to reconstruct an image.

The remaining aspects of the method complete the reconstruction. The FAT method models the object to be imaged as a collection of point scatterers in which acoustic energy scattered by each individual point does not scatter off other point scatterers. By neglecting the effects of multiple scattering, the imaging solution is formulated for a single point scatterer independent of all other point scatterers so that the solution involving all point scatterers is a linear superposition of the results for each point scatterer.

The scattered signal from a given point in the object is sampled around the aperture scanned by the receiving transducer. For isotropic scattering, it effectively acts as a secondary point source so that the FAT method seeks to determine the location of the point source from data collected around the aperture. The scattered energy is manifested as a known time delay within the received data. For a given transmitter-receiver pair, the time delay is equal to the time it takes for the pulse to travel from the transmitter to the scattering point plus the travel time of the pulse from the scattering point to the receiver. The location of a scattering point is determined by pixelating the reconstruction region and summing received data values at offsets equal to the appropriate time delays. At each pixel, low sum values denote the absence of a scatterer and high sum values denote the presence of a scatterer, the amplitude of the resultant image being proportional to the reflective contrast of that pixel.

Thus, at block 620, for each transmitter i, the wave path $r_j(t_j)$ is computed for each receiver j. The temporal data $r_j$ are derived directly from measurements at the receiver, where $t_j$ is the time delay from the transmitter i to the pixel at point (x, y). This can be determined because the background sound speed for the tissue is known. For that pixel, this information is summed at block 624 to provide a reconstructed spatial image for that transmitter i:

$$I_i(x, y) = \sum_j r_j(t_j).$$

The complete scatterer image data are then derived at block 628 by summing over all the transmitters:

$$I(x, y) = \sum_i I_i(x, y).$$

The performance of the FAT method is dependent only on the number of transmitter-receiver pairs and on the number of reconstruction pixels. It is a noniterative method that performs a simple summation at each pixel, and its speed depends on the ability of the processor to address the required $r_j(t_j)$ for each sum.

b. Quantitative Full Aperture Tomography ("QFAT")

Figure 7A:
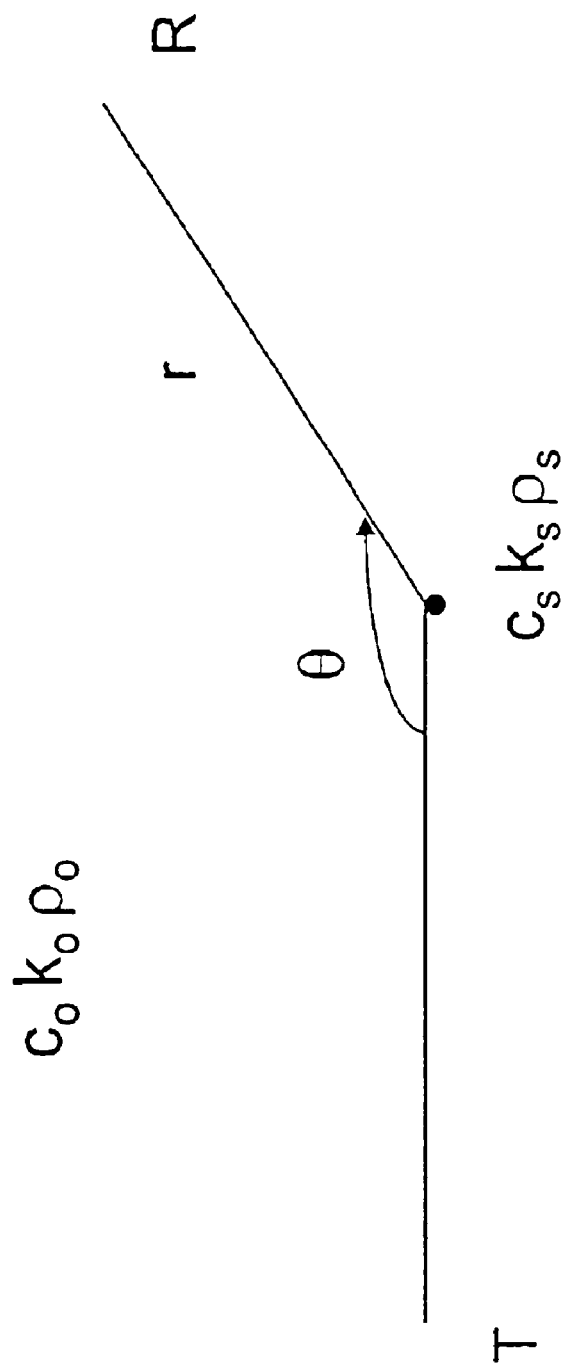
FIG. 7A illustrates the geometry used as part of a quantitative full-aperture tomographic reconstruction technique, shown with a flow diagram in FIG. 7B.

As described above, the FAT algorithm determines intensity at pixelated positions in the insonified object by backpropagating spherically expanding waves. A variation of the method, illustrated for a specific embodiment in FIGS. 7A and 7B, may be used to derive quantitative information that defines physical properties of the insonified object. For the geometry shown in FIG. 7A, a wave is transmitted by transmitter T, which is then scattered by angle θ and travels a distance r where it is detected by receiver R. For a spherical scatterer that is small compared with the wavelength of the wave, the intensity at the scatterer $P_s$ is related to the intensity of the surrounding medium $P_0$ by $$P_s = P_0 \left( \frac{\kappa_s - \kappa_0}{\kappa_0} + 3 \frac{\rho_s - \rho_0}{2\rho_s + \rho_0} \cos\theta \right) \frac{e^{ik_0 r}}{r}.$$

In this expression, a subscript "0" is used to denote physical quantities of the surrounding medium and a subscript "s" is used to denote physical quantities at the scatterer. The compressibility κ and density ρ are related to the sound speed c by $c = 1/\sqrt{\kappa \rho}$. The wave number of the surrounding medium is denoted by $k_0$.

It is evident from the above equation that the radial and angular dependencies of the intensity with respect to the scatterer differ, and this fact is exploited in the QFAT algorithm to determine physical properties. It will be appreciated that while the method is illustrated for specific physical properties and for coordinates r and θ that the method is more generally applicable for any physical properties that are expressed to vary differently according to different dimensions.

Figure 7B:
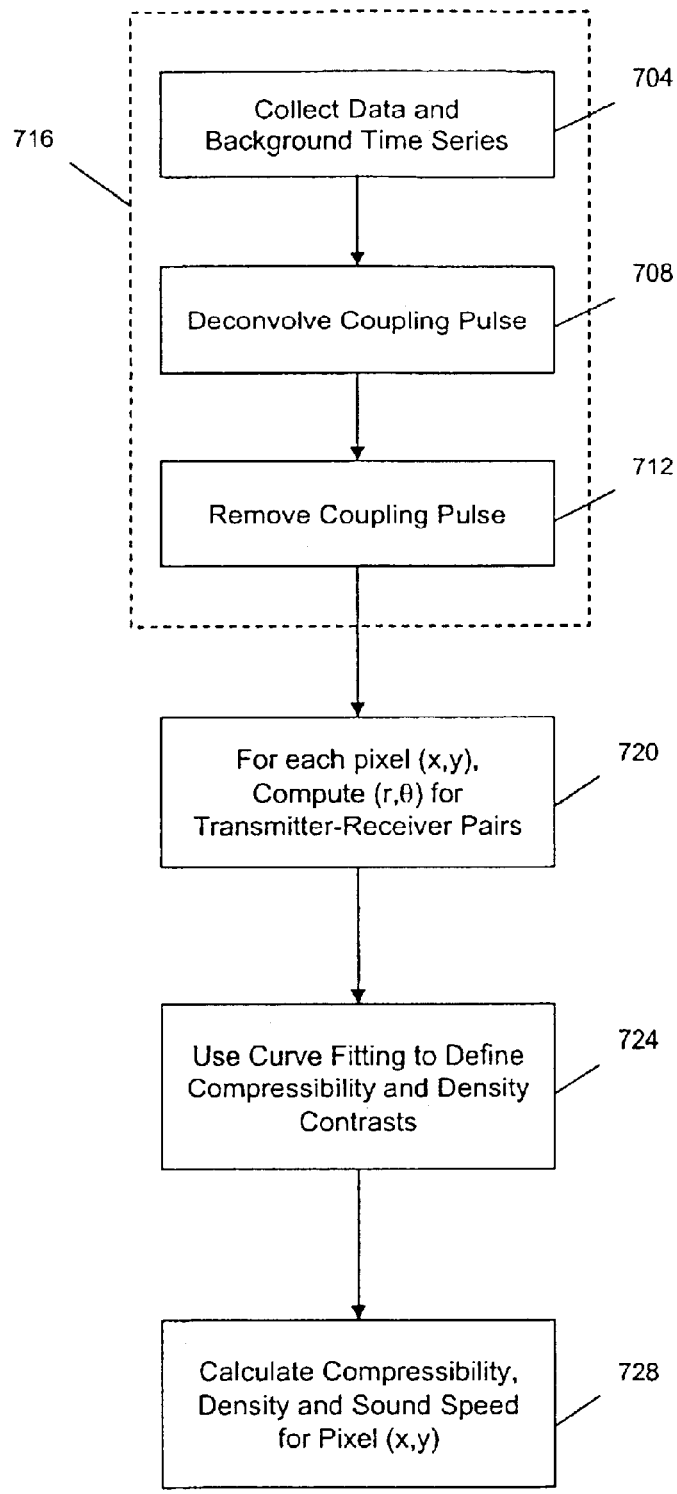

Thus, FIG. 7B provides an example of the method used to determine such physical quantities for the collected data. Block 716, as for the FAT algorithm, includes aspects of the method that are performed by the front-end electronics element 416 as part of the preprocessing function 216 discussed with respect to FIG. 2. Data time series and background time series are collected at block 704. The direct coupling pulse is deconvolved at block 708 and removed at block 712. The resulting time-series data is thereby analyzed by the remainder of the method.

The insonified object is pixelated for analysis, with individual pixels being identified by their physical coordinates (x, y). At block 720, the values of r and θ are computed for various transmitter-receiver pairs for a particular pixel located at (x, y). If no scatterer is present at that pixel, so that $\kappa_s = \kappa_0$ and $\rho_s = \rho_0$, the wave simply falls off as $e^{ik_0 r}/r$ so that there is no angular dependence. In any event, the plurality of transmitters T and receivers R define a body of (r, θ) data that follow an expected relative behavior but have independent, unknown coefficients. At block 724, a curve-fitting technique is used to determine the coefficients, which in the illustrated embodiment correspond to the compressibility contrast $(\kappa_s - \kappa_0)/\kappa_0$ and the density contrast $3(\rho_s - \rho_0)/(2\rho_s + \rho_0)$. Any suitable curve-fitting technique may be used, including polynomial and spline fitting techniques, for example.

Once the coefficients are known, the particular physical parameters of interest are calculated at block 728. For example, in the specific embodiment where breast tissue is to be examined, the surrounding-medium compressibility $\kappa_0$ and density $\rho_0$ are known, thereby providing the compressibility, density, and sound speed at (x, y). Such calculations are repeated for each pixel position to derive a distribution of such physical quantities for the entire insonified object.

In different embodiments, the compressibility may be determined in different ways. For example, in one embodiment, the tissue is insonified in a first state and a first set of measurements taken as described above. The tissue is subsequently compressed mechanically and then insonified again to provide a second set of measurements, with the compressibility being determined by comparing results from the first and second sets of measurements. In another embodiment, the tissue is also insonified in a first state and a first set of measurements taken. The tissue is subsequently insonified at a different frequency with another source, with that insonification acting to cause compression, and a second set of measurements taken. The two sets of measurements are again compared in determining the compressibility.

c. Diffraction Tomography ("DT")

Quantitative physical information may also be obtained with other techniques, such as diffraction tomography, which provides an example of a frequency-based algorithm. Briefly, the technique exploits the generalized projection-slice theorem, which states that the Fourier components of a set of receiver waveforms from a given transmitter are equivalent to the spatial Fourier components of the reconstructed image that lie on an arc in the spectral domain. After obtaining the Fourier components, then, they are interpolated onto a grid, taking into account the phase differences caused by such interpolation. In one embodiment, the grid comprises a rectangular grid. An inverse Fourier transform produces the reconstructed image.

Figure 8A:
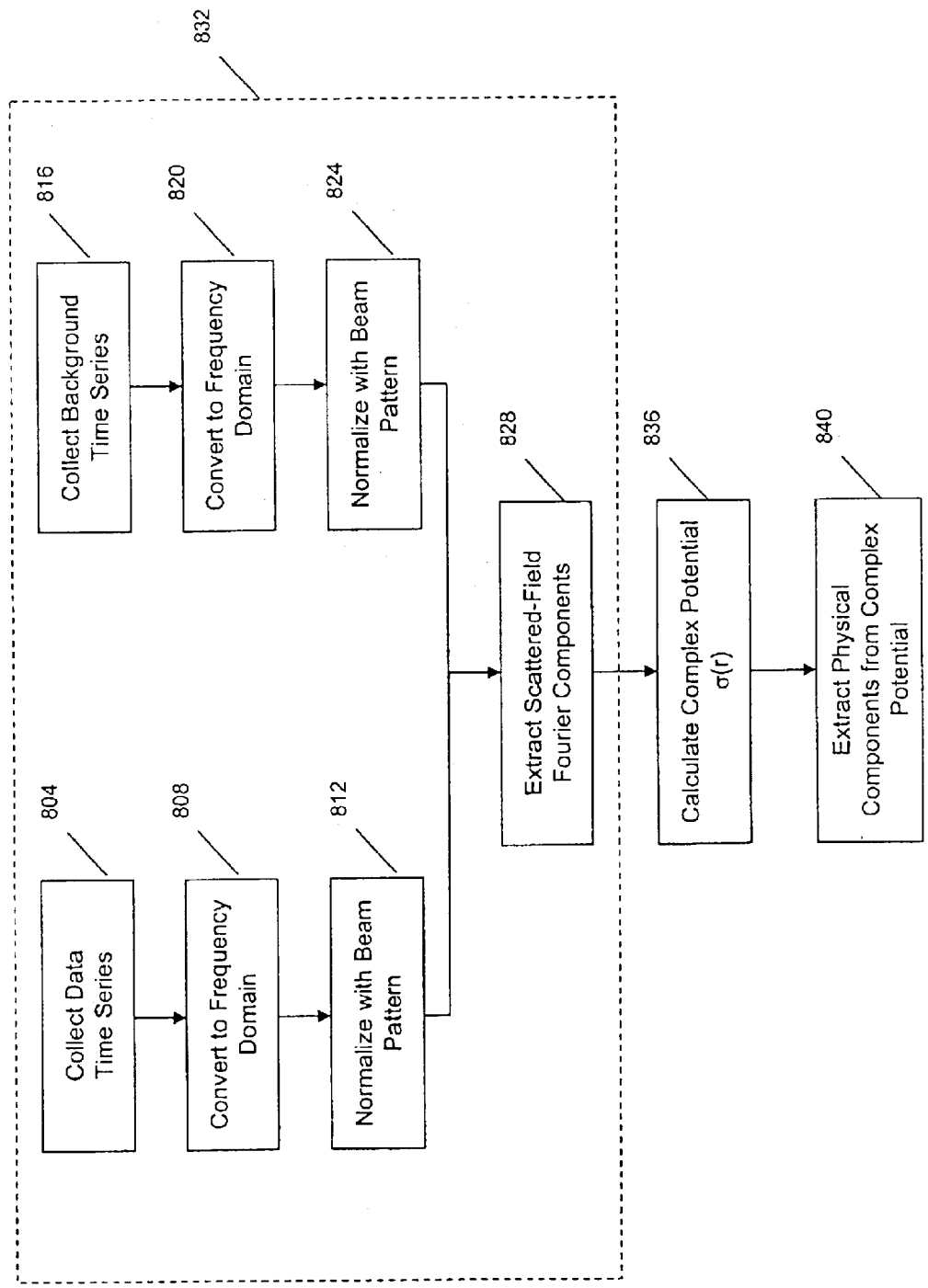
FIG. 8A is a flow diagram illustrating a diffraction tomographic reconstruction technique.

One embodiment is illustrated in detail in FIG. 8A. Those aspects of the method that are included within block 832 are aspects that in one embodiment are performed by the front-end electronics element 416 as part of the preprocessing function 216 discussed with respect to FIG. 2. Data time series and background time series are collected respectively at blocks 804 and 816. These time series are converted to the frequency domain respectively at blocks 808 and 820 according to any suitable method. One appropriate method comprises performing a fast Fourier transform on the time series. At blocks 812 and 824, the frequency-domain data are normalized with the beam pattern so that scattered-field Fourier components may be extracted at block 828.

The scattered-field Fourier components define the scattered field $P_s$, which results after the originally incident field $P_i$ is scattered by the insonified object. In one embodiment, the incident field $P_i$ comprises cylindrical or spherical waves. The incident and scattered fields may be related according to the Born approximation by the Green function $G(\Delta r, \omega)$:

$$P_s(r,\omega) = \int dr' \sigma(r') P_i(r',\omega) G(r-r',\omega),$$

where $\sigma(r)$ is the complex potential. The complex potential may be expressed in terms of the complex-wave number k and density ρ:

$$\sigma(r) = k^2(r) - k_0^2 - \sqrt{\rho(r)} \nabla^2 \frac{1}{\sqrt{\rho(r)}},$$

with the complex wave number k itself being defined in terms of the frequency ω, the sound speed c(r), and the attenuation α(r):

$$k(r) = \frac{\omega}{c(r)} + i\alpha(r).$$

At block 836, the complex potential σ(r) is calculated from the above relationships. In many embodiments, such a calculation is performed numerically, although for certain configurations of the transmitters T and receivers R, it may be performed analytically. One example that is amenable to analytic calculation comprises a circular array of transmitters T and receivers R, for which a solution of the Born approximation is presented in Michael P. Andre et al., *Acoustical Imaging*, 21, 379 (1995) and Michael P. Andre et al., *Int'l J. of Imaging Systems and Technology*, 8, 137 (1997), the entire disclosures of which are herein incorporated by reference for all purposes. At block 840, physical parameters are extracted from the complex potential σ(r):

$$c(r) = \frac{\omega}{\text{Re}\left(\sqrt{k^2(r) + \sigma(r)}\right)}$$

$$\alpha(r) = \text{Im}\left(\sqrt{k^2(r) + \sigma(r)}\right).$$

Like the FAT algorithm, the DT algorithm is a single-step process requiring no iteration so that it can be performed relatively efficiently. In the specific embodiment described, the method produces the physical quantities of sound speed and attenuation throughout the insonified object.

While the calculation performed for block 836 has been illustrated for a relationship between the incident and scattered fields that satisfies the Born approximation, a variety of alternative relationships may also be used. For example, embodiments that use the Born approximation are suitable for the analysis of media in which $(c_s - c_0)/c_0 \ll 1$. In an alternative embodiment, which corresponds to application of the Rytov approximation, the scattered field $P_s$ is substituted with $P_i \ln(P_s/P_i)$ and is suitable for the analysis of media in which changes in sound speed are small over a single wavelength of the ultrasound waves:

$$P_i(r,\omega) \ln \frac{P_s(r,\omega)}{P_i(r,\omega)} = \int dr' \sigma(r') P_i(r',\omega) G(r-r',\omega).$$

Again, in one embodiment, the incident field $P_i$ comprises cylindrical or spherical waves.

Figure 8B:
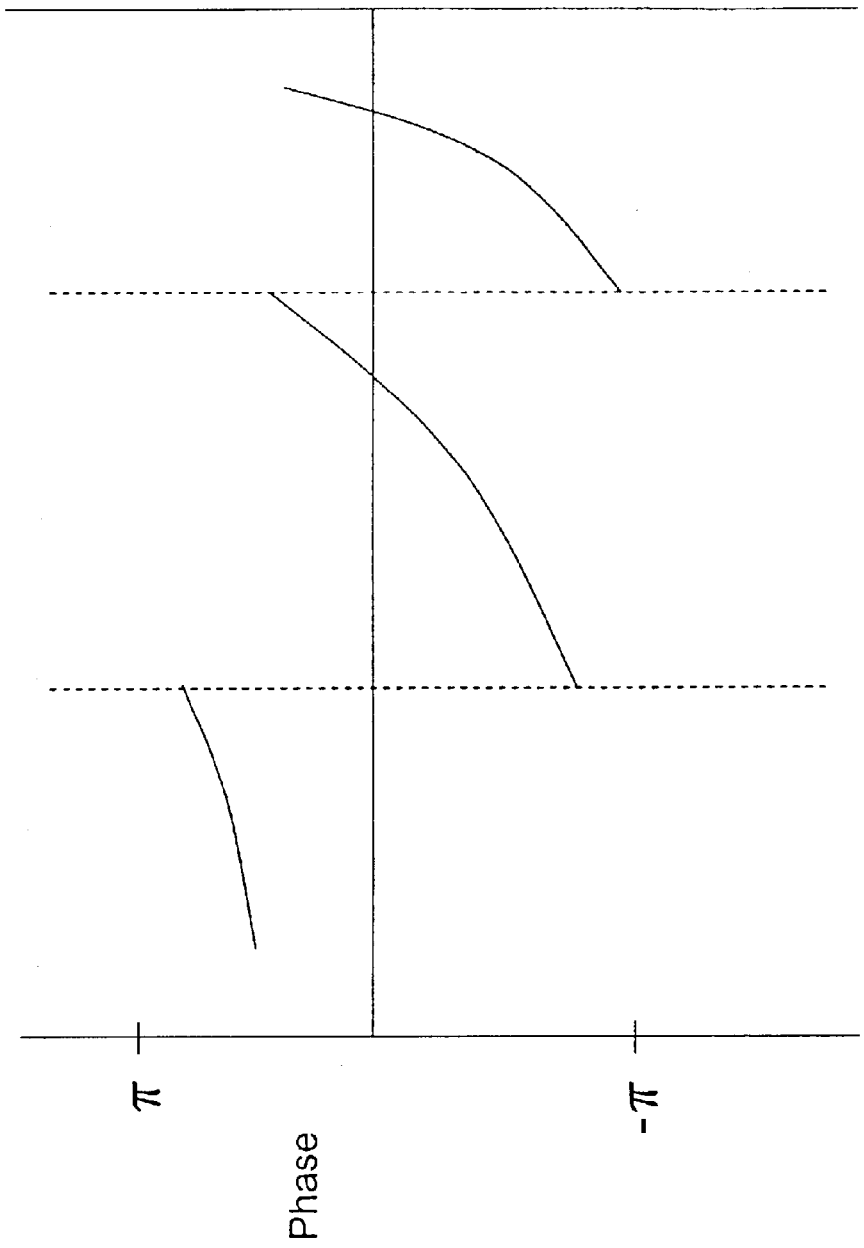
FIG. 8B illustrates a phase discontinuity that may arise in certain tomographic reconstructions.

It will be appreciated that application of the Rytov approximation with the method illustrated in FIG. 8A presents a need to unwrap phases during calculation of the logarithm. Specifically, since the fields $P_i$ and $P_s$ are generally complex, the phase of the logarithm will appear to be discontinuous when restricted to a $2\pi$ interval, such as $[-\pi, \pi)$, that corresponds to the phases of a circle. An example of this apparent discontinuity is illustrated in FIG. 8B. The general problem of phase unwrapping arises since the sequence of complex numbers represents a continuous physical quantity so that the phases outside the usual $2\pi$ interval are meaningful. Unwrapping the phase thus comprises stepping through the function shown generically in FIG. 8B, adding multiples of $2\pi$ as necessary to generate a phase sequence that reflects the continuity of the measured physical quantity.

Figures 8C, 8D:
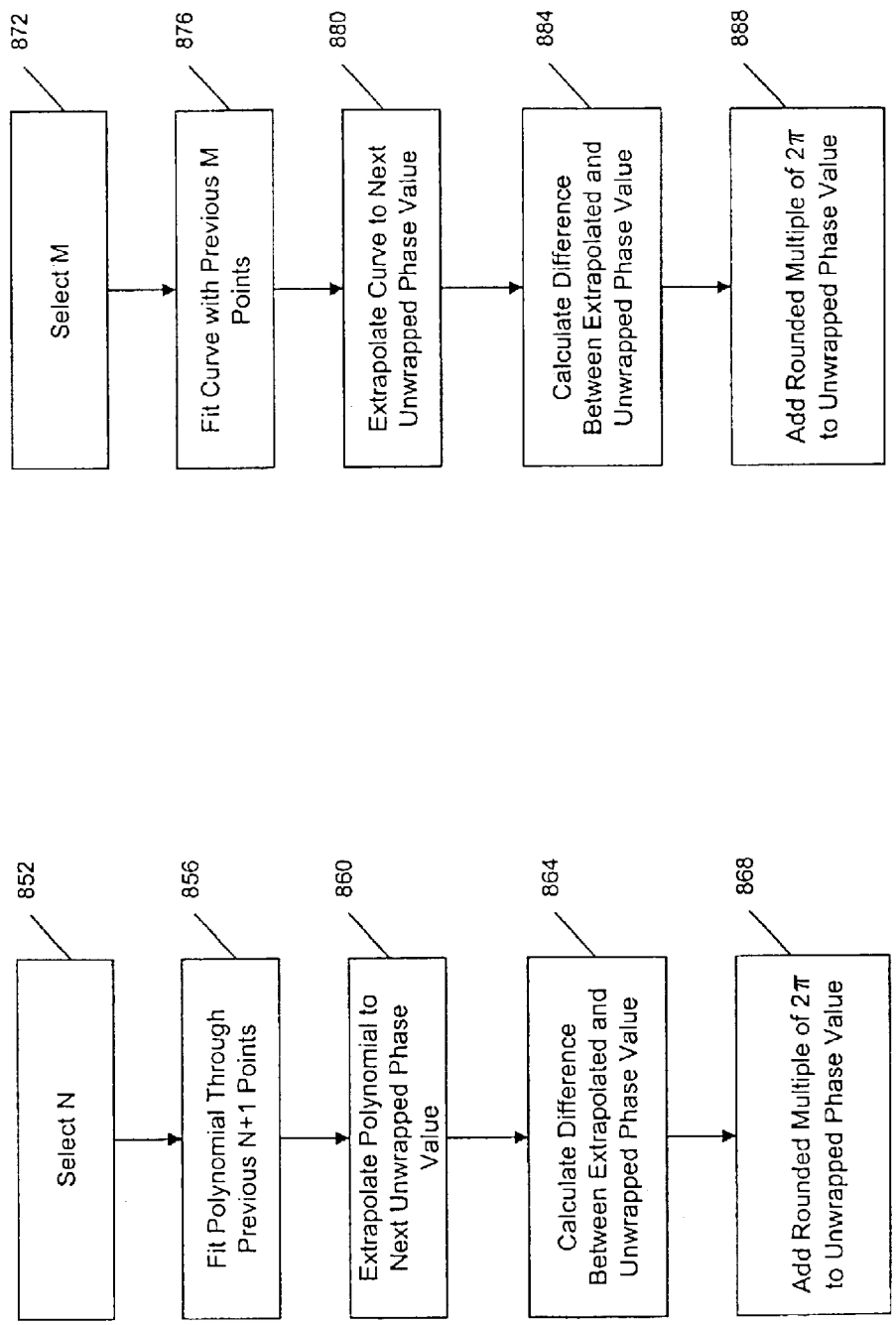
FIGS. 8C and 8D are flow diagrams illustrating methods for phase unwrapping.

Two exemplary embodiments for unwrapping the phase are shown in FIGS. 8C and 8D. In the embodiment illustrated by FIG. 8C, the phase is unwrapped by enforcing continuity of the phase sequence and all derivatives up to a specified order. The number of orders N for which continuity is to be enforced is selected at block 852. An order-N polynomial is fit through the previous N+1 points in the phase sequence at block 856, such a polynomial being uniquely defined. The polynomial fit is extrapolated to the next unwrapped phase value at block 860 so that it the extrapolated value may be compared with the actual unwrapped phase value. Accordingly, the difference between the extrapolated and unwrapped phase values is calculated at block 864. At block 868, this difference is rounded to the nearest multiple of $2\pi$, which is then added to the unwrapped phase value.

In the embodiment illustrated by FIG. 8D, the appropriate $2\pi$ multiple to be added to the unwrapped phase value is instead determined by fitting a curve to a set of M points, the fitted curve not necessarily passing through all of the points. Thus, at block 872, the number of points M to be included in the set is selected. At block 876, the curve is fit with the previous M points using any suitable curve-fitting technique. In one embodiment, such a fit comprises a least-squares polynomial fit of order N(<M-1). In another embodiment, the fit comprises a spline fit. At block 880, the curve is extrapolated to the next unwrapped phase value. At block 884, the difference between the extrapolated and unwrapped phase values is calculated. At block 888, this difference is rounded to the nearest multiple of $2\pi$, which is then added to the unwrapped phase value.

d. Full-Wave Adjoint Tomography ("FWAT")

The previously described embodiments for performing the reconstruction have illustrated single-pass methods, which have an advantage that they can be performed relatively quickly. Another class of embodiments comprises iterative methods, which typically include a built-in accuracy check and therefore have the advantage that the accuracy of the results may be better understood. One such iterative embodiment comprises a full-wave adjoint tomographic method, which is illustrated with the flow diagram of FIG. 9. Briefly, the method exploits an operator representation for using the Helmholtz equation $(\nabla^2+k^2)P=0$ to estimate the field P scattered through the insonified object, and using the adjoint operator to approximate the inverse operation. Such a combination provides a good trade-off between accuracy and computational efficiency of the inverse operation.

The full-wave adjoint tomographic technique may be understood by defining the quantities used in the model: (1) hypothesized physical parameters q, which define the physical characteristics of the insonified object according to the model; (2) wave propagation operator $\hat{R}$, which defines how an acoustic wave propagates within the model; and (3) simulated data q, which defines measurable quantities as they are computed within the model. Each of these model quantities has a corresponding real physical quantity: (1) real physical parameters $\underline{q}$, which define the actual physical characteristics of the insonified object that are sought by the method; (2) real wave propagation operator $\underline{\hat{R}}$, which defines the actual physical process acting on the acoustic wave; and (3) measured data $\underline{g}$, which defines the quantities that are actually measured. The method essentially seeks to reproduce the physical process $\underline{g}=\underline{R}\underline{q}$ with the simulated process g=Rq, by comparing how accurately g can be made to reproduce $\underline{g}$. The simulation uses a wave-propagation model represented by $\hat{R}$ chosen to be as close to $\underline{\hat{R}}$ as possible from external results, but does not specifically seek to determine $\underline{\hat{R}}$ itself. Backpropagation as described below is then achieved in the reproduction with the adjoint operator $\hat{R}^\dagger$. For example, an acceptable model may be a first-cut image produced by the diffraction algorithm, which provides an initial image that can be an acceptable starting point for the adjoint algorithm. A theoretical description of this technique may be found in F. Natterer, "A Propagation-Backpropagation Method for Ultrasound Tomography," *Inverse Problems* 11, 1225–1232 (1995), the entire disclosure of which is herein incorporated by reference for all purposes.

Figure 9:
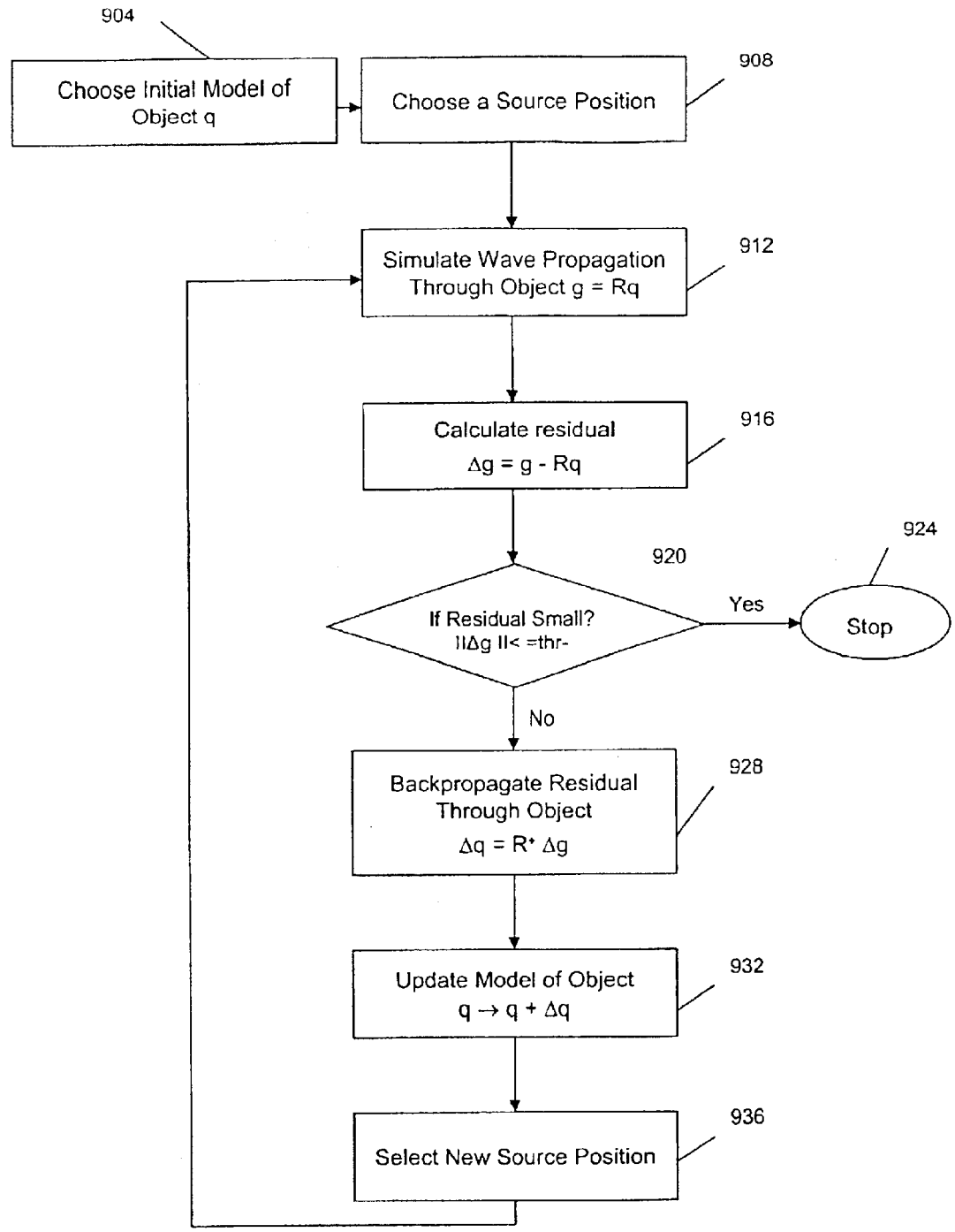
FIG. 9 is a flow diagram illustrating a full-wave adjoint tomographic reconstruction technique.

Thus, in at block 904 in FIG. 9, the method begins by choosing an initial model of the insonified object q. Such an initial model may, in principle, be selected by any appropriate technique, although convergence of the iterative method is expected to be more rapid for a more accurate initial model. Thus, in certain embodiments, the initial model is determined with a single-pass analysis of the measured data $\underline{g}$. As part of its iterative quality, the method may vary a source position with each iteration. Thus, at block 908, an initial source position is chosen. At block 912, the simulated data are calculated for the model physical parameters and source wave by using the simulation to propagate the source wave through the object to determine simulated data: g=Rq.

The simulated data g are compared with the measured data $\underline{g}$ at blocks 916 and 920. First, the residual $\Delta g=\underline{g}-Rq$ is calculated at block 916. The residual is a measure of how closely the data sets match, and is accordingly also a measure of how accurate the hypothesized physical parameters q match the real physical parameters $\underline{q}$. Thus, at block 920, the magnitude of the residual is evaluated to determine whether it is smaller than a predetermined threshold value. If it is, the method is considered to have converged to the desired accuracy and stops at block 924. If it is not, an additional iteration is performed.

The additional iteration begins at block 928, where the residual is backpropagated through the object: $\Delta q=R^\dagger\Delta g$. Such backpropagation effectively seeks to estimate the degree to which hypothesized and real physical parameters differ. Thus, the hypothesized parameters are corrected at block 932 according to the back-propagated results: $q \rightarrow q+\Delta q$. With these new hypothesized parameters, the method is iterated back to block 912 after selecting a new source position. In this manner, the hypothesized physical parameters q tend to converge to the real physical parameters $\underline{q}$, with the method accounting for the different source positions.

Further details regarding the application of such FWAT methods to imaging techniques is described in U.S. Pat. No. 6,005,916, entitled "APPARATUS AND METHOD FOR IMAGING WITH WAVEFIELDS USING INVERSE SCATTERING TECHNIQUES," issued Dec. 21, 1999, the entire disclosure of which is herein incorporated by reference for all purposes.

e. Migration Algorithm

In another embodiment, a migration algorithm is used, the goal of which is to determine the shape and position of a reflecting boundary be measuring the arrival times of the reflected waves. The reflected waves are registered for every position of the excitation source at one or more points at the surface S that lies above the medium. For a sound transmitter with coordinates $(X_K, Y_K)$ on a surface S and a receiver with coordinates $(x_k, y_k)$, the arrival time of the reflected wave n is $t_n = F(K_K, Y_K, x_k, y_k)$. The migration transformation is aimed at constructing an element of the reflecting boundary in the vicinity of each excitation source, i.e. to determine the depth $Z_n(x_i, y_i)$ at which the reflecting boundary is located. The detailed information of the shape and the position of the reflecting boundary is obtained by making measurements at many points along the surface S.

There are many ways of performing a migration transformation that are within the scope of the invention. In any given instance, the choice of preferred algorithm may depend on the complexity of the object under investigation—its morphology, the acoustical contrast of its boundaries, etc. In some embodiments, the preferred migration algorithm is based on diffraction-like transformations in which each point at the reflecting boundary is treated as a secondary source of spherical diffracted waves (Huygens principle). A travel time for a wave from the sound source to the point where the diffraction occurs and the position where it is registered is determined by the arrival time of the reflected wave. The dynamic characteristics of the reflected wave in this process play only a secondary role. The accuracy of the obtained envelope as a representation of the reflecting boundary in question is improved as the number of positions of a sound transmitter is increased in the reconstruction of such surfaces.

In one embodiment, the determination of the specific characteristics of the migration transformation is made in accordance with the following: (1) for the objects under investigation, the longitudinal sound waves are most important; (2) the speed differentiation of all objects is small, with the refraction coefficients lying in the interval [0.95, 1.05], thereby allowing multiple reflections in all diffraction processes to be neglected; (3) the average sound speed in all objects is known to better than about 5% accuracy; (4) the acoustic field includes reflected and diffracted waves, as well as direct (transmitted) waves, which are considered to be regular noise; (5) the signal-to-noise ratio is sufficiently high to perform a deconvolution transformation, thereby increasing the resolution of the method by a factor of 1.5 to 2.0; (6) the shape of the excitation pulse is known and stable; (7) the directionality of the sound transmitters and receivers is such that the objects are effectively two-dimensional; and (8) the locus of measurements is a closed curve with the objects located inside the boundary defined by the locus. Thus, in the specific embodiment using the migration transformation, wave traces exist for a fixed set of angle offsets for all positions of the sound transmitter. They form a set of N wave traces for every angle offset along a circular profile. Each of the wave traces permits construction of a position of the reflecting boundary. By increasing the number of the wave traces, the accuracy of positioning the reflecting boundary and its diffracting properties are improved.

f. Full-Wave Tomography ("FWT")

Another iterative method that is similar in some respects to FWAT is full-wave tomography. This method is described in detail in U.S. Pat. No. 5,588,032, entitled "Apparatus and method for imaging with wavefields using inverse scattering techniques," issued to Steven A. Johnson on Dec. 24, 1996, the entire disclosure of which is herein incorporated by reference for all purposes. In particular, FIG. 8 of that patent sets forth a flow diagram of the method.

6. Operation

The system described above may be operated in a number of distinct ways in different embodiments to provide different types of data for analysis. In one embodiment, a single ultrasound analysis is performed. A plurality of pulsed spherical or cylindrical ultrasound waves are propagated into tissue using the ultrasound transmission elements described above. In one embodiment, the ultrasound waves comprise a frequency between 0.5 and 2.0 MHz. The ultrasound radiation is scattered from the tissue, where such scattering includes a mixture of transmission and reflection of waves. A mixture of reflected and transmitted ultrasound waves are accordingly received by the ultrasound receiving elements described above. A representation of the tissue is subsequently generated from the received scattered ultrasound radiation.

In another embodiment, a combination of ultrasound and electromagnetic radiation is used to generate the representation of the tissue. Such an embodiment may be derived from a sensor system described above that is configured for simultaneous electromagnetic irradiation of tissue such as is used for mammography and for acoustic irradiation of the tissue. The nature of the two types of radiation is such that the acoustic radiation will typically be scattered from the tissue while the electromagnetic radiation will propagate through the tissue.

Figure 10A:
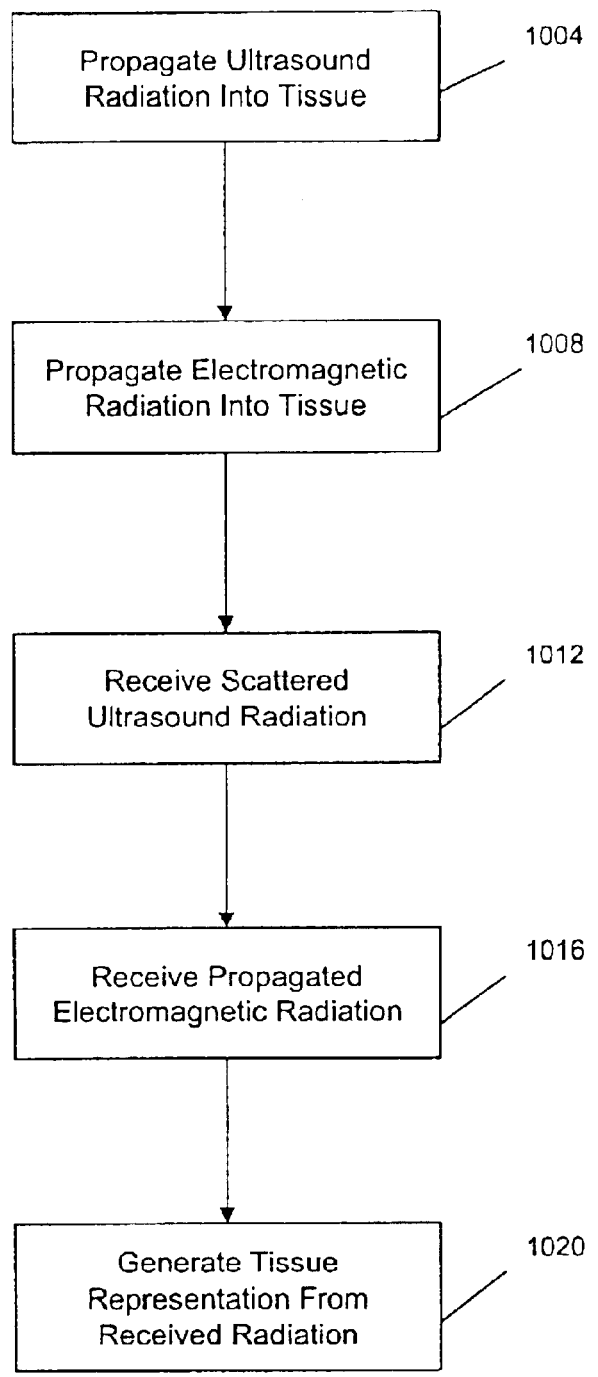
FIG. 10A is a flow diagram illustrating an embodiment that uses acoustic and electromagnetic imaging simultaneously.

An example of such an embodiment is provided with the flow diagram of FIG. 10A. At block 1004, the ultrasound radiation is propagated into the tissue and at block 1008, the electromagnetic radiation is propagated into the tissue. At blocks 1012 and 1016 respectively, the scattered acoustic radiation and propagated electromagnetic radiation are received. At block 1020, the tissue representation is generated from the received radiation. The representation of the tissue thus comprises a simultaneous rendering of the acoustic data and the electromagnetic data. The simultaneous presentation of acoustic and electromagnetic data renderings not only provides additional information that may be used by a practitioner diagnostically, but also facilitates a transition by a practitioner from relying on mammographic data to also using acoustic imaging.

Figure 10B:
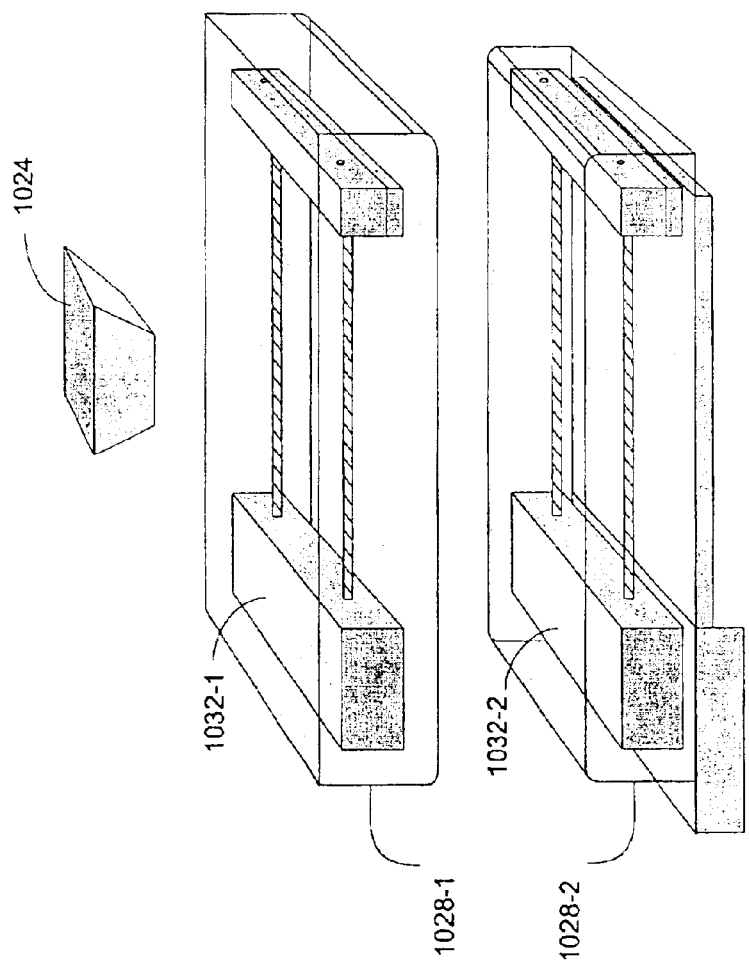
FIG. 10B is a perspective view of one embodiment of the sensor system configured for simultaneous acoustic and electromagnetic imaging.

Current mammography equipment has been designed for mediolateral-oblique ("MLO") and cranial-caudal ("CC") imaging, both of which may be adapted to perform simultaneous acoustic and electromagnetic renderings. An example of an embodiment that uses a paddle arrangement is illustrated in FIG. 10B. Two paddles 1028 are provided that comprise acoustic arrays 1032 as described above. In addition, an x-ray electromagnetic source 1024 is provided with an x-ray sensor 1036. In order to accommodate the electromagnetic imaging, the paddles 1028 are further configured such that the carriage assembly may be retracted from the field of view defined by the x-ray image. In one embodiment, the x-ray sensor 1036 may comprise a photographic film, but in another embodiment comprises a digital x-ray sensor. Where the x-ray sensor 1036 comprises a digital x-ray sensor, the x-ray images may be combined with the acoustic images in a single display.

In a specific embodiment, the acoustic and electromagnetic data renderings are overlaid so that information from a single physical region of the tissue may be viewed for both sources. While a mammogram provides a superimposed view through the entire thickness of the tissue, a three-dimensional acoustic image may be windowed to show narrow slices that are parallel to the plane of the mammogram. A practitioner may thus use the system to scroll through distinct slices of the acoustic rendering in the direction orthogonal to the mammogram plane. The resulting combination is an acoustically enhanced mammogram that may focus on specific slices of the tissue and may display acoustic characteristics on the mammogram. In one embodiment, an x-ray mammogram is enhanced by highlighting all tissue that is more absorbing than a particular duct wall, say 5% more absorbing, since this may be diagnostically relevant.

Figure 10C:
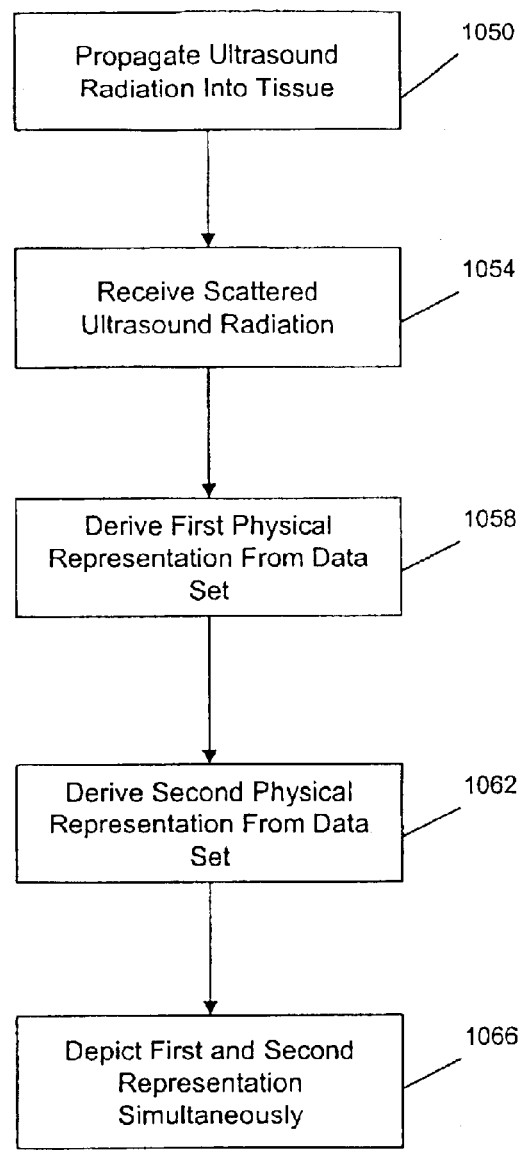
FIG. 10C is a flow diagram illustrating multimodal acoustic imaging.

In a further embodiment, multimodal acoustic diagnostics may be performed. An example that permits such multimodality is illustrated in FIG. 10C. At block 1050, ultrasound radiation is propagated into tissue, such as by the system described above. Ultrasound radiation scattered by the tissue is received at block 1054. From this single data set, first and second physical representations are derived respectively at blocks 1058 and 1062.

In one specific embodiment, the two physical representations may be derived using different tomographic reconstruction algorithms, including each of those described above, i.e. full-aperture tomography, quantitative full-aperture tomography, diffraction tomography, full-wave adjoint tomography, acoustic tomography, and full-wave tomography. The use of different algorithms to reconstruct images from the same data may produce different sets of images containing different and complementary information. This exploits the fact that the scattered radiation that is received contains more information than is used by any one reconstruction algorithm.

In a second specific embodiment, the two physical representations are derived by using different frequencies from the waveform rather than applying different tomographic reconstruction algorithms. This again provides increased information.

Another representation may be derived from dynamic pressure scanning, which uses potential alterations of multiple ultrasound parameters due to physical compression of the sensor paddles. This differs from static elastography in which stress and strain (Young's modulus) are recorded when a compressible object is reduced in volume within a closed space since even a slight increase in compression with the paddle geometry would not control lateral volume expansion. Instead, changes in sound speed, attenuation, reflectivity, and blood flow may result from variation in the application of direct pressure at the scan site. It has been confirmed, for example, that an otherwise isoechoic mass in the prostate becomes more hypoechoic, as characterized by reduced backscatter coefficient and reflectivity, when an end-fire prostate probe applies direct pressure upon the prostate surface. Similarly, experience with malignant and benign breast masses demonstrates increases in the Doppler flow patterns with lighter scanning pressure. Significant dynamic information may also be provided by sound speed, attenuation, and compressibility. Accordingly, in some embodiments, the system described above is used to provide operator-independent tumor vascularity assessment from multiple angles to provide a further representation.

In other specific embodiments, the two physical representations may be derived using different types of reconstruction techniques. These types may differ significantly in the type of data that are used for the reconstruction. For example, while FIG. 10A illustrated the combined use of electromagnetic and acoustic radiation, other embodiments of the invention may combine techniques acoustic techniques with impedance-measurement techniques, fat-suppression imaging techniques, or other diagnostic techniques. Examples of impedance-measurement techniques that may be combined with other techniques as described herein are provided in copending, commonly assigned U.S. patent application Ser. No. 09/794,612, entitled "MULTI-DIMENSIONAL BIOELECTRICAL TISSUE ANALYZER," filed Feb. 27, 2001 by Peter J. Littrup et al., the entire disclosure of which is incorporated herein by reference for all purposes. Examples of fat-suppression imaging techniques that may be combined with other techniques as described herein are provided in copending, commonly assigned U.S. Prov. Pat. Appl. No. 60/381,022, entitled "METHOD AND APPARATUS FOR COMBINED DIAGNOSTIC AND THERAPEUTIC ULTRASOUND SYSTEM INCORPORATING NONINVASIVE THERMOMETRY, ABLATION CONTROL AND AUTOMATION," filed May 16, 2002 by Peter J. Littrup, the entire disclosure of which is incorporated herein by reference for all purposes. The fat-suppression imaging techniques described therein may themselves use sound-speed information from a variety of different algorithms, including those described above. Sound speed easily differentiates fat from other tissue and may significantly reduce data requirements for contour analysis and identification of masses, architectural distortion, and/or clustered microcalcifications. In addition, analysis of other parameters such as vascular flow may be used and, in some instances, limited to a smaller tissue volume that does not contain fat.

Figure 11:
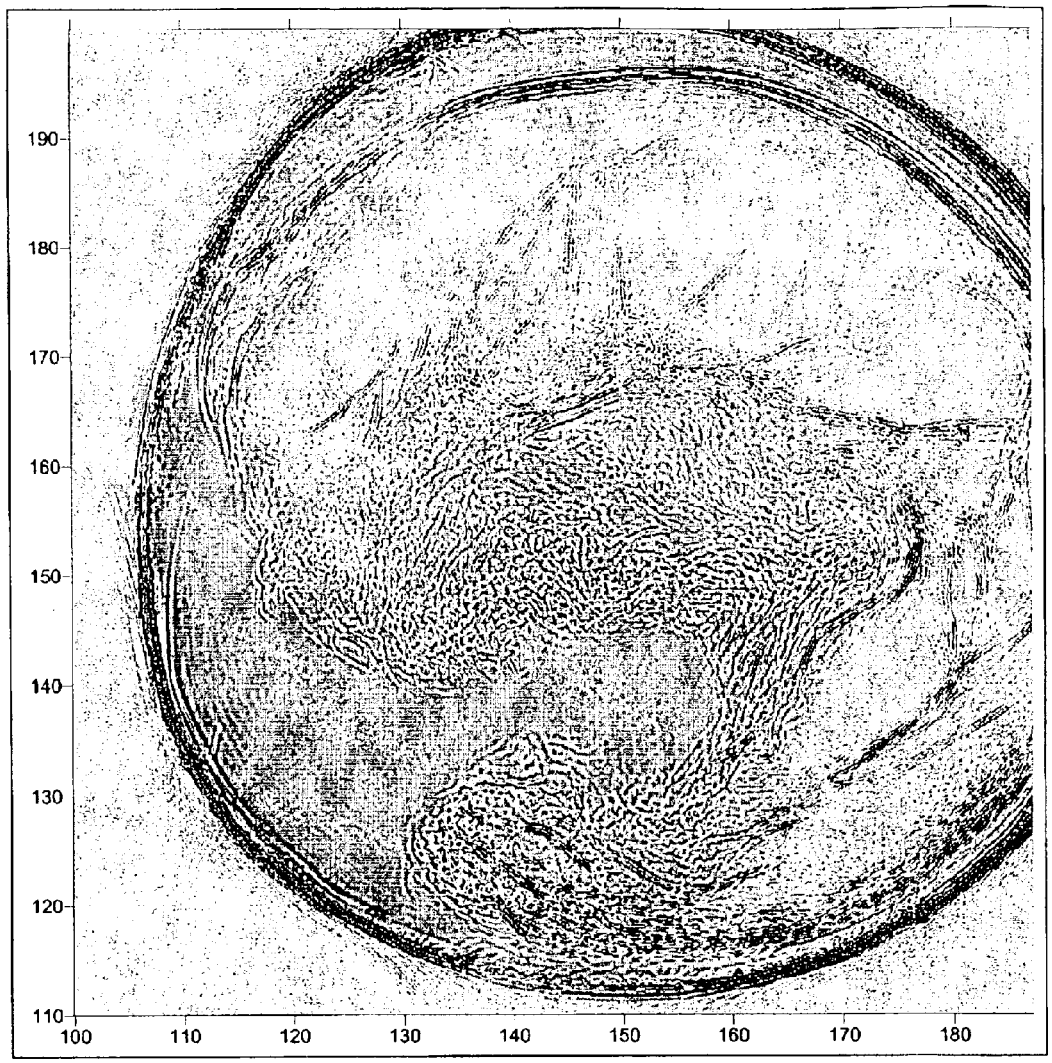
FIG. 11 is an example of an image illustrating results of a multimodal method.

Accordingly, at block 1066, the first and second representations are depicted simultaneously to provide the practitioner with the increased level of available information. An example of such a result is provided in FIG. 11, which provides results simultaneously showing reflection and sound speed for a human breast. The reflection data are shown with solid lines in the figure, permitting the discernment of boundaries within the breast and sound speed is shown in color, with red indicating higher sound speeds and blue indicating lower sound speeds. While this technique has been illustrated using first and second representations, it will be appreciated that an even greater number of representations may be used, such as by providing simultaneous depictions of three, four, five, or even more representations in different embodiments.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for investigating tissue, the method comprising:

receiving acoustic data derived from scattering a plurality of pulsed spherical or cylindrical acoustic waves from a plurality of transmission elements through the tissue to a plurality of receiving elements, wherein the received acoustic data include a mix of reflected and transmitted acoustic waves;

digitizing the acoustic data; and generating a representation of a portion of the tissue from the digitized acoustic data, wherein generating the representation of the portion of the tissue from the digitized acoustic data comprises removing a direct coupling pulse from the received acoustic data.

2. The method recited in claim 1 wherein generating the representation of the portion of the tissue from the digitized acoustic data comprises performing a time-series analysis of the digitized acoustic data.

3. The method recited in claim 1 wherein generating the representation of the portion of the tissue from the digitized acoustic data comprises performing a frequency-series analysis of the digitized acoustic data.

4. The method recited in claim 1 wherein generating the representation of the portion of the tissue from the digitized acoustic data comprises:
for each pair of transmitting and receiving elements, computing a wave path from a time delay; and
summing such wave paths to derive an image representation of the portion of the tissue.

5. The method recited in claim 1 wherein generating the representation of the portion of the tissue from the digitized acoustic data comprises:
organizing the digitized acoustic data according to at least two independent dimensions; and
numerically fitting the digitized data to an expression relating the expected intensity variation in terms of physical quantities having different dependencies in the at least two independent dimensions.

6. The method recited in claim 5 wherein the physical quantities comprise a compressibility contrast and a density contrast.

7. The method recited in claim 1 wherein generating the representation of the portion of the tissue from the digitized acoustic data comprises:
converting the digitized acoustic data to a frequency domain;
extracting scattered-field Fourier components from the converted data;
calculating a complex potential from a scattered field defined by the scattered-field Fourier components; and
deriving physical properties of the portion of the tissue from the complex potential.

8. The method recited in claim 7 wherein the physical properties comprise a sound speed and an attenuation.

9. The method recited in claim 1 wherein generating the representation of the portion of the tissue from the digitized acoustic data comprises:
(a) initially choosing a tissue model of the portion of the tissue;
(b) simulating wave propagation of the pulsed spherical or cylindrical waves through the tissue model with a wave-propagation model to determine simulated data;
(c) backpropagating a residual derived from comparing the simulated data with the digitized acoustic data through an adjoint of the wave-propagation model to update the tissue model; and
(d) repeating (b) and (c) until a magnitude of the residual is less than a predefined threshold.

10. The method recited in claim 1 wherein:
the acoustic data comprise a first set of acoustic data measured from a first insonification of the tissue and a second set of acoustic data measured from a second insonification of the tissue; and
generating the representation comprises determining a compressibility of the tissue from the first and second sets of acoustic data.

11. The method recited in claim 10 wherein measurements of the first and second sets of acoustic data are separated by a mechanical compression of the tissue.

12. The method recited in claim 10 wherein the second insonification causes a compression of the tissue.

13. The method recited in claim 1 wherein:
the acoustic data comprise a first set of acoustic data measured from a first insonification of the tissue under a first compression mode and a second set of acoustic data measured from a second insonification of the tissue under a second compression mode; and
generating the representation comprises determining an acoustic property of the tissue correlated with a difference between the first and second compression modes.

14. The method recited in claim 13 wherein the acoustic property comprises a property selected from the group consisting of sound speed, attenuation, density, compressibility, absorption, acoustic impedance change, and blood flow rate.

15. A method for investigating tissue, the method comprising:
receiving acoustic data derived from scattering a radiation pattern of acoustic waves from a plurality of transmission elements to a plurality of receiving elements, wherein the received acoustic data include a mix of reflected and transmitted acoustic waves;
digitizing the acoustic data;
organizing the digitized data according to at least two independent dimensions; and
numerically fitting the digitized data to an expression relating the expected intensity variation in terms of physical quantities having different dependencies in the at least two independent dimensions.

16. The method recited in claim 15 wherein the physical quantities comprise a compressibility contrast and a density contrast.

17. The method recited in claim 16 wherein the at least two dimensions comprise a radial dimension and an angular dimension, and wherein the compressibility contrast does not vary with the angular dimension.

18. The method recited in claim 17 wherein the expression comprises $$P_s = P_0 \left( \frac{\kappa_s - \kappa_0}{\kappa_0} + 3 \frac{\rho_s - \rho_0}{2\rho_s + \rho_0} \cos\theta \right) \frac{e^{ik_0 r}}{r},$$

wherein r is the radial dimension, $\theta$ is the angular dimension, $\kappa_s$ is a compressibility of a feature within the tissue, $\rho_s$ is a density of the feature, $P_s$ is an intensity of the feature within the tissue, $\kappa_0$ is a compressibility of a region surrounding the feature, $\rho_0$ is a density of the region surrounding the feature, $k_0$ is a wave number of the region surrounding the feature, and $P_0$ is an intensity of the region surrounding the feature.

19. A method for investigating tissue, the method comprising:
receiving scattered acoustic data derived from scattering an initial acoustic radiation pattern from the tissue, wherein the received scattered acoustic data include a mix of reflected and transmitted acoustic waves;
digitizing the received acoustic data and the initial acoustic radiation pattern;
converting the digitized received acoustic data and the digitized initial acoustic radiation pattern to a frequency domain;
extracting scattered-field components by comparing the converted digitized received acoustic data with the converted initial acoustic radiation pattern;
calculating a complex potential from the scattered-field components; and
deriving physical properties of a portion of the tissue from the complex potential.

20. The method recited in claim 19 wherein calculating the complex potential comprises solving a scattering equation within a Born approximation.

21. The method recited in claim 19 wherein calculating the complex potential comprises solving a scattering equation within a Rytov approximation.

22. The method recited in claim 19 wherein calculating the complex potential comprises unwrapping a phase.

23. The method recited in claim 22 wherein unwrapping the phase comprises:

fitting an Nth-order polynomial through N+1 unwrapped phase values;

extrapolating the polynomial to a subsequent unwrapped phase value to determine an extrapolated value;

calculating a difference between the extrapolated value and the subsequent unwrapped phase value; and adding a rounded multiple of $2\pi$ to the subsequent unwrapped phase value.

24. The method recited in claim 22 wherein unwrapping the phase comprises:

fitting a curve with M unwrapped phase values;

extrapolating the curve to a subsequent unwrapped phase value to determine an extrapolated value;

calculating a difference between the extrapolated value and the subsequent unwrapped phase value; and adding a rounded multiple of $2\pi$ to the subsequent unwrapped phase value.

25. The method recited in claim 24 wherein the curve comprises an Nth order polynomial with $N<M-1$.

26. The method recited in claim 24 wherein the curve comprises a spline.

27. A method for investigating tissue, the method comprising:

(a) initially choosing a tissue model for a portion of the tissue;

(b) initially choosing a source position;

(c) simulating, for the source position, propagation of an acoustic radiation pattern through the tissue model with a wave-propagation model to determine simulated data;

(d) backpropagating a residual derived from comparing the simulated data with a set of measured data derived by propagating the acoustic radiation pattern through the portion of the tissue physically through an adjoint of the wave-propagation model to update the tissue model, wherein the set of measured data includes a mix of reflected and transmitted acoustic waves;

(e) selecting a new source position; and (f) repeating (c)–(e) until a magnitude of the residual is less than a predefined threshold.

28. The method recited in claim 27 wherein initially choosing a tissue model comprises performing a full-aperture tomographic analysis of the set of measured data.

29. The method recited in claim 27 wherein initially choosing a tissue model comprises performing a diffraction tomographic analysis of the set of measured data.

30. A method for unwrapping a phase of a function acting on a complex quantity, the method comprising:

fitting an Nth-order polynomial through N+1 unwrapped phase values;

extrapolating the polynomial to a subsequent unwrapped phase value to determine an extrapolated value;

calculating a difference between the extrapolated value and the subsequent unwrapped phase value; and adding a rounded multiple of $2\pi$ to the subsequent unwrapped phase value.

31. A method for unwrapping a phase of a function acting on a complex quantity, the method comprising:

fitting a curve with M unwrapped phase values;

extrapolating the curve to a subsequent unwrapped phase value to determine an extrapolated value;

calculating a difference between the extrapolated value and the subsequent unwrapped phase value; and adding a multiple of $2\pi$ to the unwrapped phase value.

32. The method recited in claim 31 wherein the curve comprises an Nth-order polynomial with $N<M-1$.

* * * * *